(12) United States Patent
Hayes et al.

(10) Patent No.: US 8,071,143 B2
(45) Date of Patent: Dec. 6, 2011

(54) METHODS FOR THE TREATMENT OR PREVENTION OF DIABETES MELLITUS AND OTHER METABOLIC IMBALANCES

(75) Inventors: Kenneth C. Hayes, Wellesley Hills, MA (US); Kalyana Sundram, Petaling Jaya (MY); Ravigadevi Sambanthamurthi, Petaling Jaya (MY); Yew Ai Tan, Taman Cheras (MY)

(73) Assignees: Brandeis University, Waltham, MA (US); Malaysian Palm Oil Board, Selangor, Kajang (MY)

( * ) Notice: Subject to any disclaimer, the term of this patent is extended or adjusted under 35 U.S.C. 154(b) by 492 days.

(21) Appl. No.: 12/080,361

(22) Filed: Apr. 2, 2008

(65) Prior Publication Data
US 2009/0252817 A1 Oct. 8, 2009

(51) Int. Cl.
A61K 36/00 (2006.01)
A61K 47/00 (2006.01)
(52) U.S. Cl. .................. 424/777; 424/725; 424/439
(58) Field of Classification Search ............... None
See application file for complete search history.

(56) References Cited

U.S. PATENT DOCUMENTS

| | | | |
|---|---|---|---|
| 6,156,738 A * | 12/2000 | Bell et al. ............. | 514/60 |
| 6,881,854 B2 | 4/2005 | Ptock et al. | |
| 2003/0031740 A1 | 2/2003 | Sambanthamurthi et al. | |
| 2008/0193603 A1 * | 8/2008 | Hayes et al. ............. | 426/74 |

OTHER PUBLICATIONS

Elaeis guineenis Jacq. (Source James A Duke, 1983. Handbook of Energy Crops and website aricle www.hort.purdue.edu/newcrop/duke_energy/elaeis_guineensid.html).*
Harris et al. (Extraction and Identification of Water-Soluble Compounds in Palm-Pressed Fiber, American Journal of Environmental Sciences 3 (2): 54-59, 2007).*
Abeywardena et al., "Polyphenol-enrished extract of oil palm fronds (Elaeis guineenis) promotes vascular relaxation via endothelium-dependent mechanisms," Asia Pacific Journal Clin. Nutr., vol. 11 (Suppl), 2002, pp. S467-S472.
Archibald, "Antioxidant Products: Nutritional Science and Marketplace Opportunities," Prepared Foods 2007, May supplement [retrieved on Feb. 4, 2009]. Retrieved from the Internet: <URL: <http://files.bnpmedia.com/PF/Home/Files/PDFs/AntioxSupp.pdf>>.
Attele et al., "Antidiabetic Effects of Panax ginseng Berry Extract and the Identification of an Effective Component," Diabetes, vol. 51, Jun. 2002, pp. 1851-1858.
Aucott et al., "Weight loss in obese diabetic and non-diabetic individuals and long-term diabetes outcomes—a systematic review," Diabetes, Obesity and Metabolism, vol. 6, 2004, pp. 85-94.
Aviram et al., "Pomegranate juice consumption reduces oxidative stress, atherogenic modifications to LDL, and platelet aggregation: studies in humans and in atherosclerotic apolipoprotein E-deficient mice," Am J Clin Nutr, vol. 71, 2000, pp. 1062-1076.

Broadhurst, et al., "Insulin-like biological activity of culinary and medicinal plant aqueous extracts in vitro," J. Agric. Food Chem. 2000, 48(3), pp. 849-852.
El-Alfy et al., "Protective effect of red grape seeds proanthocyanidins against induction of diabetes by alloxan in rats," Pharmacological Research, vol. 52, 2005, pp. 264-270.
Hayes, et al., "The complex interplay of palm oil fatty acids on blood lipids," Eur. J. Lipid Sci. Technol. 2007, 109(4), pp. 453-464.
Hosoda et al., "Antihyperglycemic Effect of Oolong Tea in Type 2 Diabetes," Diabetes Care, vol. 26, No. 6, Jun. 2003, pp. 1714-1718.
Lakka et al., "The Metabolic Syndrome and Total and Cardiovascular Disease Mortality in Middle-aged Men," JAMA, vol. 288, No. 21, Dec. 4, 2002, pp. 2709-2716.
Ludvik et al., "Efficacy of Ipomoea batatas (Caiapo) on Diabetes Control in Type 2 Diabetic Subjects Treated With Diet," Diabetes Care, vol. 27, No. 2, Feb. 2004, pp. 436-440.
Refinetti, "The Nile Grass Rat as a Laboratory Animal," Lab Animal, vol. 33, No. 9, Oct. 2004, pp. 54-57.
Singh et al., "Attenuation of hyperglycemia and associated biochemical parameters in STZ-induced diabetic rats by dietary supplementation of potato peel powder," Clinica Chimica Acta, vol. 353, 2005, pp. 165-175.
Tan et al., "Valorisation of palm by-products as functional components," Eur. J. Lipid Sci. Technol., vol. 109, 2007, pp. 380-393.
Wu et al., "Green tea supplementation ameliorates insulin resistance and increases glucose transporter IV content in a fructose-fed rat model," European Journal of Nutrition, vol. 43, No. 2, 2004, pp. 116-124.
Xie et al., "American Ginseng Berry Juice Intake Reduces Blood Glucose and Body Weight in ob/ob Mice," Journal of Food Science, vol. 72, No. 8, 2007, pp. S590-S594.
Zunino et al., "Diets Rich in Polyphenols and Vitamin A Inhibit the Development of Type I Autoimmune Diabetes in Nonobese Diabetic Mice," The Journal of Nutrition, vol. 137, 2007, pp. 1216-1221.
Balasundram, Nagendran, et al., "Antioxidants from palm (Elaeis guineensis) fruit extracts," Asia Pac. J. Clin. Nutr., vol. 12, Suppl. S37 (2003).
Wu, Shu-Jing, et al., "Antioxidant and Antihepatoma Activities of Palm Oil Extract," Journal of Food Lipids, vol. 14, pp. 122-137 (2007).
International Search Report for PCT/US2009/039296 mailed Oct. 30, 2009.
Extended European Search Report dated May 4, 2011 from EP 09 755 464.6. Edem, D.O., "Palm oil: Biochemical, physiological, nutritional, hematological, and toxicological aspects: A review," Plant Foods for Human Nutrition, 57:319-341 (2002).
Nazaimoon et al., "Palm Vitamin E Reduced Serum Levels of Glycated Hemoglobin, Advanced Glycosylation End-Products and Malondialehyde of STZ-Induced Diabetic Rats," Diabetes Research and Clinical Practice, Amsterdam, NL, XP009147576, 50(1):S357 (2000).

* cited by examiner

Primary Examiner — Christopher R Tate
Assistant Examiner — Randall Winston
(74) Attorney, Agent, or Firm — Foley Hoag, LLP

(57) ABSTRACT

The invention relates to methods for treatment and prevention of a metabolic imbalance, including diabetes mellitus and other related diseases or disorders, using an extract from a fruit of genus Elaeis.

16 Claims, 28 Drawing Sheets

Fasting blood glucose in Nile rats up to 12 months of age

Fewer animals survive to 50 wks, and those that do have a lesser degree of hyperglycemia (diabetes)

Random blood glucose vs water intake in male Nile Rats developing spontaneous diabetes Measurements from 23 male Nile rats 20-32 weeks old.

FIG. 7
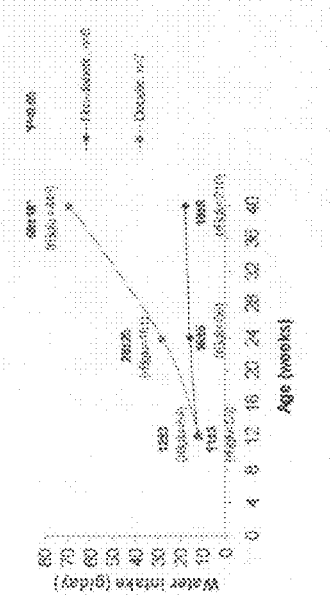
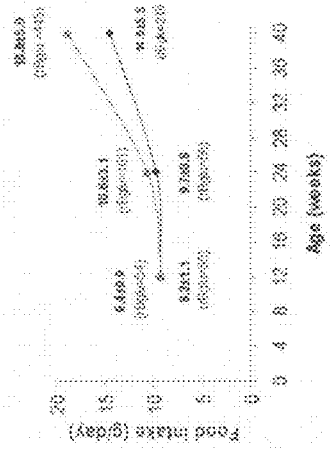
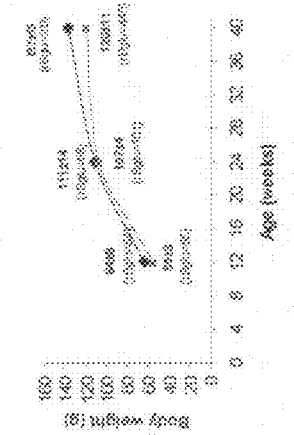
Male Nile rats demonstrate increased food and water intake associated with rising blood glucose among the first signs of Type 2 diabetes. Excess body weight (adipose) is not a prerequisite to diabetes onset. n=13

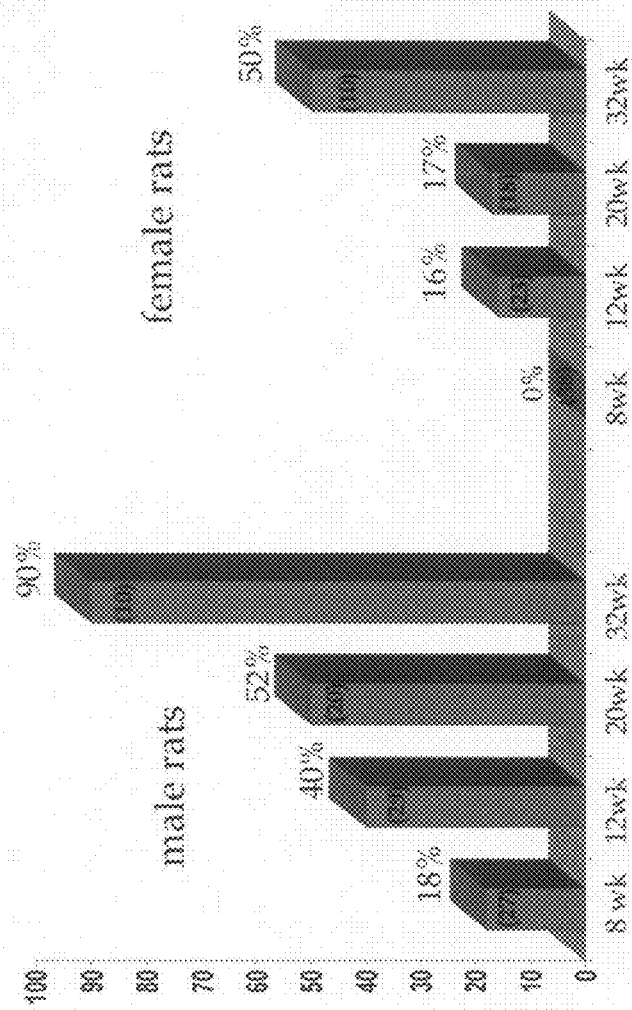

FIG. 9

Food and water intake for nondiabetic and diabetic Nile rats

| Group | Food intake kcal/day ($\bar{x} \pm SD$) | Caloric Index (kcal/g BW) ($\bar{x} \pm SD$) | Water intake ml/day ($\bar{x} \pm SD$) |
|---|---|---|---|
| Nondiabetic* (n=13) | 60 ± 18 | 519 ± 160 | 14 ± 9 |
| Diabetic (n=12) | 96 ± 30** | 861 ± 289** | 81 ± 17** |

*Nondiabetic fasting glucose averaged about 65mg/dl from mix of 12wk and 52wk males and females, whereas Diabetics had fasting blood glucose about 160mg/dl.

**Significantly greater in diabetics (P<0.05) using Student's t-test. In essence, diabetics waste calories.

FIG. 12  Lipoprotein analysis for fasted control and diabetic Nile rats

| | Nondiabetic (n=5) | Prediabetic (n=7) | Diabetic (n=6) |
|---|---|---|---|
| Glucose* (mg/dl) | 48±8[b] | 115±28[a] | 596±373[a,b] |
| VLDL-C absolute (mg/dl) | 12±5[b] | 22±13[a] | 558±335[a,b] |
| VLDL-C - percentage | 10±2[b] | 18±13[a] | 70±14[a,b] |
| LDL-C -absolute (mg/dl) | 26±9[b] | 39±12[a] | 163±94[a,b] |
| LDL-C - percentage | 23±3 | 29±5 | 24±18 |
| HDL-C absolute (mg/dl) | 76±17 | 72±37 | 41±35 |
| HDL-C - percentage | 67±4[b] | 51±16[a] | 6±5[a,b] |
| LDL-C/HDL-C | 0.34±0.06 | 0.60±0.21 | 8.9±9.4 |
| TC | 114±30[b] | 137±38[a] | 762±377[a,b] |
| TC/HDL-C | 1.5±0.09[b] | 2.0±0.58[a] | 29.0±18[a,b] |
| TG | 69±0.27[b] | 90±45[a] | 2340±1758[a,b] | a,b,c.. Means in a row sharing a common superscript are significantly different (p<0.05) using one-way ANOVA and Fisher's PLSD test.

Liver Weight in Nile rats developing diabetes

FIG. 14

Average insulin values for Nile rats at different levels of fasting glucose

| Glucose Group (mg/dl) | Fasting Blood Glucose, mg/dl ($\bar{x} \pm SD$) | Fasting Insulin, ng/ml ($\bar{x} \pm SD$) |
|---|---|---|
| <60 (n=12) | 46 ± 8 | 2.1 ± 2.4 |
| 61-110 (n=10) | 77 ± 12 | 2.4 ± 1.4 |
| 111-400 (n=11) | 225 ± 96 | 5.6 ± 4.7* |
| >400 (n=4) | 426 ± 22 | 1.6 ± 0.7 |

*Includes values >12 ng/dl cutoff in assay, so the arbitrary number of 12 ng/dl was assigned.

FIG. 15

Glucose and Insulin response in male Nile rats during an ipGTT

Insulin response to 2.5 g/kg bd wt glucose injection in individual male Nile rats

| Rat number | Fast. Glucose 0' (mg/dl) | Insulin 0' (mcU/ml) | Fast. Glucose 60' | Insulin 60' | Notes |
|---|---|---|---|---|---|
| 206M | 78 | 0.9 | 491 | 9.5 | Insulin resistant |
| 194M | 413 | 0.7 | 530 | 1.4 | Poor insulin secretion |
| 193M | 287 | 2 | 505 | 0.9 | Poor insulin secretion |
| m58M | 40 | 0.5 | 89 | 0.7 | Normal |
| 119M | 47 | 7.6 | 411 | >12.3 | Insulin resistant |
| 114M | 41 | 1.5 | 90 | 7 | Early resistance |
| 108M | 127 | 1.6 | 394 | 5.6 | Insulin resistant |
| 98M | 71 | 1.6 | 177 | 3.8 | Early resistance |
| 97M | 454 | 2.3 | 738 | 2.9 | Poor insulin secretion |

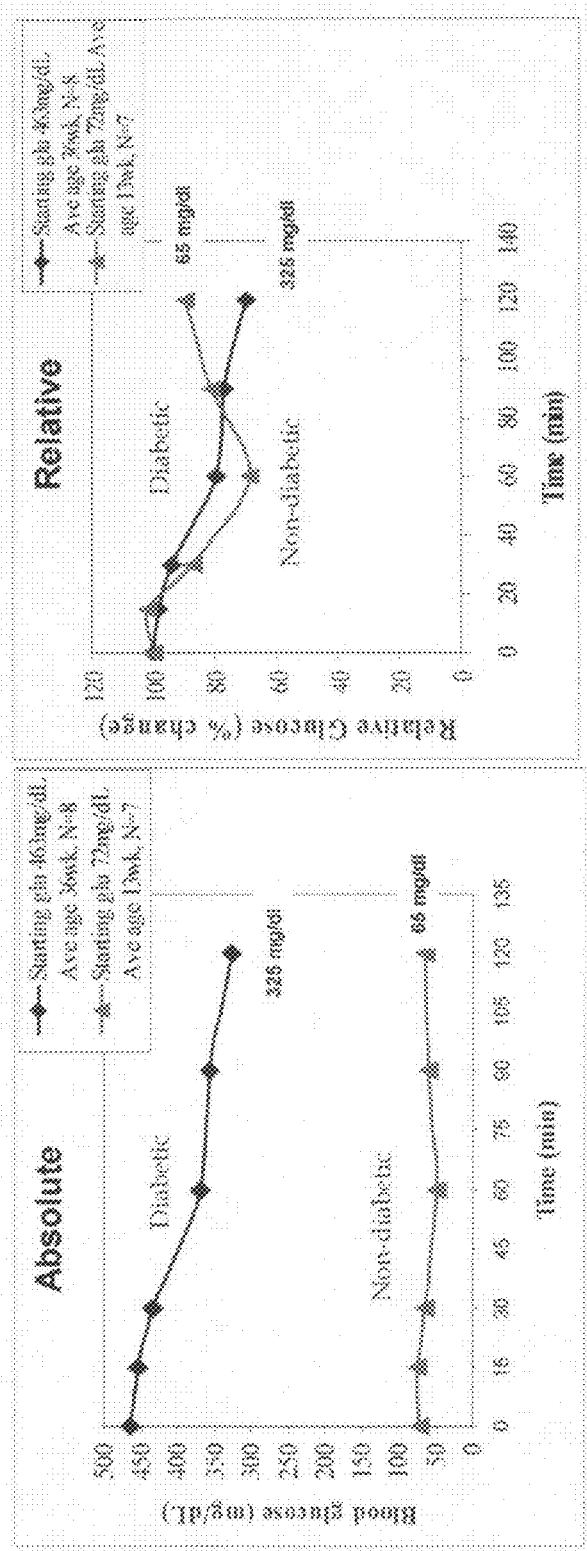
FIG. 17 Absolute and relative glucose response to IP insulin ITT in diabetic versus nondiabetic Nile rats (nonfasting)

FIG. 18

Body Mass Index and Lean Mass Index for diabetic and nondiabetic female Nile rats fed high-fat and low-fat diets

| | High-fat Diet @ 45%en ($\bar{x} \pm SD$) | Low-fat Diet @ 10%en ($\bar{x} \pm SD$) |
|---|---|---|
| Initial fasting blood glucose (mg/dl) | 116±119 | 118±94 |
| Final fasting glucose after 12 wks (mg/dl) | 223*±125 | 82*±19 |
| BMI (kg/m²) after 12 wks | 5.8±10.4 | 6.0±0.3 |
| LMI (kg/m²) after 12 wks | 3.6±0.2 | 3.9±0.2 |

*Significantly different (P<0.05) using one-way ANOVA and Fisher's PLSD test. (n=4)

FIG. 19

Body and organ weights, blood glucose and plasma lipids in 5wk old male Nile rats fed 3 types of diets for 5 months

| | Low-fat/<br>hi-fiber | Hi-fat/<br>low-fiber | (Chow-5008) |
|---|---|---|---|
| CHO:FAT:PROT %en | 69:15:16 | 40:43:17 | 67:11:22 |
| Body weight (g) | | | |
| Initial (5 weeks old) | 51±3 | 52±7 | 55±5 |
| Final (5 mo on diet) | 110±11 | 118±19 | 131±9 |
| Body wt gain (g/d) | 0.34±0.06 | 0.38±0.09 | 0.41±0.07 |
| Food intake as dry diet (g/d) | 22±1.5 | 14±1.0 | N/A |
| (kcal/d) | 79±5 | 64±4 | N/A |
| Food efficiency index (kcal/g gain/d) | 232±15 | 168±11 | N/A |
| Blood glucose (mg/dl) | | | |
| Random, after 8wk | 395±149[a] | 276±82 | 150±82[a] |
| Fasting, terminal 23 wk | 76±17 | 158±114 | 118±142 | a,b,c.. *Means in a row sharing a common superscript are significantly different ($p<0.05$) using one-way ANOVA and Fisher's PLSD test.*
*Blood glucose after 15h fast, 24wk old (n=5/group)*

FIG. 20

Plasma and liver lipids in 5 wk old male Nile rats fed 3 types of diets for 5 months

|  | Low-fat/hi-fiber | Hi-fat/low-fiber | (Chow-5008) |
|---|---|---|---|
| Plasma (fasting, terminal*) | | | |
| TC (mg/dL) | 199±51 | 568±400$^a$ | 97±14$^a$ |
| TG (mg/dL) | 194±26$^a$ | 1371±992$^{a,b}$ | 203±78$^b$ |
| Liver Lipids | | | |
| TC (mg/g) | 3.0±0.9$^a$ | 14.7±2.6$^{a,b}$ | 4.5±1.8$^b$ |
| TG (mg/g) | 18±8$^a$ | 137±40$^{a,b}$ | 35±6$^b$ | a,b,c. Means in a row sharing a common superscript are significantly different (p<0.05) using one-way ANOVA and Fisher's PLSD test.
*Blood glucose after 15h fast, 24wk

FIG. 21

| Organ weight (%BW) | Low-fat/hi-fiber | Hi-fat/low-fiber | (Chow-5008) |
|---|---|---|---|
| Liver | 5.39±0.54[a] | 7.23±1.06[a,b] | 4.48±1.41[b] |
| Adipose | | | |
| perirenal+retroperitoneal | 0.80±0.59 | 0.73±0.62 | 1.34±0.53 |
| epididymal | 2.25±0.69 | 2.59±0.82[a] | 3.33±0.35[a] |
| inguinal | 0.73±0.42 | 0.72±0.25 | 0.85±0.15 |
| Total adipose | 3.79±1.63 | 4.04±1.64 | 5.52±0.98 |
| Kidney | 1.26±0.31 | 1.47±0.33[a] | 0.98±9.30[a] |
| Pancreas | 0.27±0.12 | 0.21±0.02 | 0.43±0.18 |
| Cecum | 3.3±0.9 | 2.1±1.0 | 2.1±1.3 |
| Spleen | 0.15±0.04 | 0.20±0.06 | 0.18±0.6 |
| Heart | 0.32±004 | 0.36±0.02[a] | 0.30±0.02[a] |
| Testes | 1.53±0.42 | 1.66±0.23 | 1.39±0.08 |
| Brain | 0.72±0.05 | 0.77±0.09 | 0.67±0.04 | a,b,c.. Means in a row sharing a common superscript are significantly different (p<0.05) using one-way ANOVA and Fisher's PLSD test.
*Blood glucose after 15h fast, 24wk. Study 2.

METHODS FOR THE TREATMENT OR PREVENTION OF DIABETES MELLITUS AND OTHER METABOLIC IMBALANCES

FIELD OF THE INVENTION

The invention relates to methods for treatment and prevention of diabetes mellitus, a pre-diabetic state, and other related disorders using oil palm fruit juice

BACKGROUND OF THE INVENTION

Diabetes mellitus is a chronic disorder of fat, carbohydrate, and protein metabolism. It is characterized by high levels of blood glucose resulting from defects in insulin production, insulin action, or both, which translates into impaired glucose transport and metabolism, resulting in hyperglycemia. The World Health Organization (WHO) estimates that over 180 million people suffer from diabetes, making it one of the most common noncommunicable diseases, and is expected to double by the year 2030.

In the United States, 20.8 million people, or approximately 7% of the population, have diabetes. An estimated 14.6 million have been diagnosed with diabetes, however, 6.2 million are unaware that they have the disease. Over 10% of adults (age 20 or older) have diabetes, while over 20% of Americans age 60 or older have the disease. Approximately 90-95% of all people diagnosed with diabetes have adult-onset, or Type 2 diabetes. The remaining 5-10% of people with diabetes (generally children and young adults) have insulin-dependent, or Type 1, diabetes. The risk of developing diabetes increases with age and body weight, commonly measured by body mass index. About 1.5 million new cases are diagnosed in adults each year. In 2002, diabetes was the sixth leading cause of death in the United States and was very likely to have been underreported. There are serious medical complications that result from having diabetes including heart disease, stroke, high blood pressure, eye complications (retinopathy, cataracts), kidney disease (nephropathy), nervous system disease (neuropathy), peripheral vascular disease, dental disease, gastroparesis, sexual dysfunction, and complications during pregnancy. Overall, the risk of death among age-matched people with diabetes is about twice that of people without diabetes.

People with Type 1 diabetes must have insulin replacement, either delivered by a pump or injection. Those with Type 2 diabetes may be able to control their blood glucose by following a careful diet and exercise program, weight loss, and/or taking oral medications. Many people with diabetes also need to take medications to control their cholesterol and blood pressure. Among adults with diagnosed diabetes, about 11% take both insulin and oral medications, 22% take insulin only, 49% take oral medications only, and 17% do not take either insulin or oral medications. Most non-insulin therapies are oral drugs designed to either lower blood glucose levels, improve the sensitivity to or increase the pancreatic secretion of insulin to postprandial glucose levels. Oral anti-diabetics account for about 63% of the total anti-diabetic drug sales. Metformin, for example, works by keeping the liver from making too much sugar, but is not efficacious for everyone, and effectiveness typically decreases over time. Another class of drugs, insulin-sensitizers or glitazones, lower insulin resistance to help a diabetic's declining levels of insulin to be more effective. However, glitazones have been associated with liver toxicity and death, so physicians remain cautious about the use of these drugs. Accordingly, there is a vast clinical need for safer and more effective therapies to treat diabetes and other related disorders.

SUMMARY OF THE INVENTION

The present invention is directed to, at least, methods and kits for treating and preventing diabetes mellitus and other metabolic imbalances.

In one embodiment, the present invention provides a method of treating a metabolic imbalance in a mammal, comprising administering to the mammal a therapeutically effective amount of an extract from a fruit of genus *Elaeis*.

In one aspect, the extract is in a nutraceutical or pharmaceutical composition. In another aspect the extract is a water-soluble component. In yet another aspect, the water-soluble extract contains phenolics. In certain aspects, the phenolics include cinnamate and benzoate derivatives. In one embodiment, the extract is from the genus *Elaeis*. In another embodiment, the extract is from the vegetation liquor of the palm oil milling process and is palm fruit juice.

In another embodiment, the method further comprises enhancing an insulin secretion and/or sensitivity. In yet another embodiment, the method further comprises reducing a blood glucose level.

In certain aspects of the invention, the metabolic imbalance is selected from the group consisting of: diabetes mellitus, gestational diabetes, genetic defects of β-cell function, genetic defects in insulin action, diseases of the exocrine pancreas, endocrinopathies, drug or chemical-induced, infections, other genetic syndromes associated with diabetes, a pre-diabetic state, and metabolic syndrome. In one aspect, the metabolic imbalance is diabetes mellitus, including type I and/or type II. In another aspect, the metabolic imbalance is Latent Autoimmune Diabetes in adults (e.g., type 1.5 diabetes).

In yet another aspect, treating diabetes mellitus in the mammal, prevents a secondary medical complication of diabetes mellitus. In still another aspect, the secondary medical complication of diabetes mellitus includes heart disease, stroke, hypertension, retinopathy, cataract, nephropathy, neuropathy, peripheral vascular disease, dental disease, gastroparesis, sexual dysfunction, and complications during pregnancy.

According to the invention, the metabolic imbalance may be a metabolic syndrome. In one aspect, treating metabolic syndrome comprises treating one or more diagnostic criteria. In yet another embodiment, the diagnostic criteria is selected from the group consisting of waist circumference, triglycerides, HDL, blood pressure, and fasting blood glucose level. In still another embodiment, the metabolic imbalance is a pre-diabetic state and the mammal has one or more risk factors for diabetes mellitus. In another aspect, the pre-diabetic state comprises impaired fasting glucose level or glucose intolerance. In yet another aspect, the one or more risk factors for diabetes mellitus is selected from the group consisting of: age, physical inactivity, abnormal BMI, genetic predisposition, ethnicity, hypertension, polycystic ovary syndrome, cardiovascular disease, previous impaired fasting glucose or glucose tolerance, and other clinical conditions associated with insulin resistance.

The invention further includes the use of kits. In one embodiment, the kit includes (a) a package comprising a composition of an extract of the vegetation liquor from the milling process of the fruit of genus *Elaeis*; and (b) instructions for use of said extract of the vegetation liquor from the milling process of the fruit of genus *Elaeis* for a treatment of a metabolic imbalance. In another embodiment, the metabolic imbalance is diabetes mellitus.

BRIEF DESCRIPTION OF THE DRAWINGS

FIG. 7 is a panel of graphs showing food intake, water intake, and body weight for male Nile rats developing Type 2 diabetes.

FIG. 8 is a bar graph showing the percentage of male and female Nile rats with a random blood glucose of greater than 200 mg/dL by age.

FIG. 9 is a chart of the food and water intake for nondiabetic and diabetic Nile rats.

FIG. 12 is a chart of the lipoprotein analysis in nondiabetic fasted control and diabetic Nile rats.

FIG. 14 is a chart of the average insulin values for Nile rats at varying fasting blood glucose levels.

FIG. 15 is a chart of the insulin response in male and female Nile rats.

FIG. 17 is a panel of two graphs showing the absolute and relative nonfasting glucose response to intraperitoneal insulin tolerance test in diabetic and nondiabetic Nile rats.

FIG. 18 is a chart of body mass index (BMI) and lean mass index (LMI) for female Nile rats fed a high or low fat diet.

FIG. 19 is a chart of body and organ weights, blood glucose profile, and caloric intake in 5 week old male Nile rats fed 3 different diets for 5 months.

FIG. 20 is a chart of plasma and liver lipids in 5 week old male Nile rats fed 3 different diets for 5 months.

FIG. 21 is a chart of organ weight in 5 week old male Nile rats fed 3 different diets for 5 months.

DETAILED DESCRIPTION OF THE INVENTION

Figure 1:
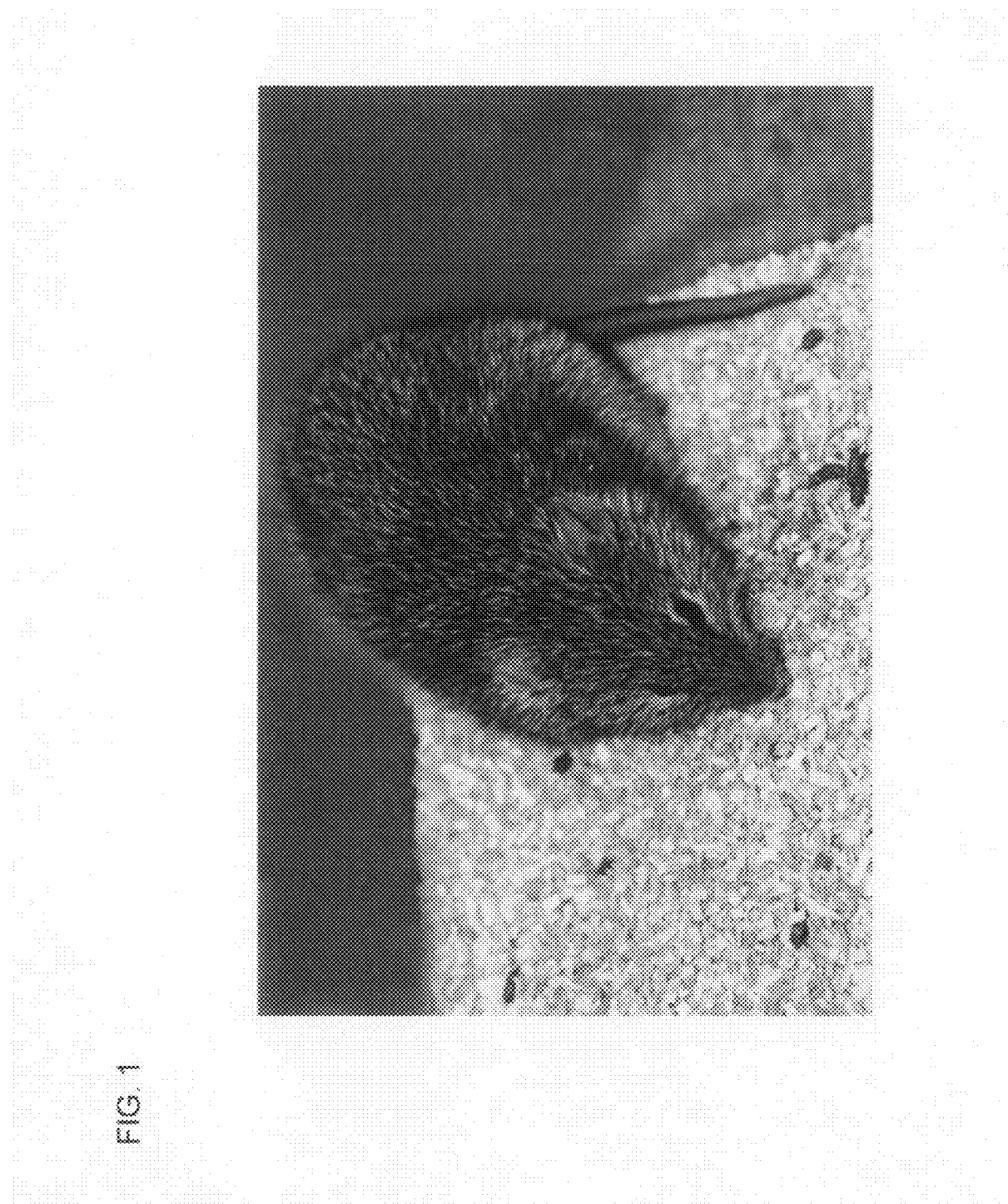
FIG. 1 is a picture of the Nile rat (*Arvicanthis niloticus*).

The disclosed description, methods, and examples facilitate treating and preventing metabolic imbalances, diabetes mellitus, a pre-diabetic state, metabolic syndrome, and other related disorders using the fruit from the oil palm.

It also relates to the treating and preventing of secondary medical complications that result from having diabetes including heart disease, stroke, high blood pressure, eye complications (retinopathy, cataracts), kidney disease (nephropathy), nervous system disease (neuropathy), peripheral vascular disease, dental disease, gastroparesis, sexual dysfunction, and complications during pregnancy.

The use of the terms "a," "an," and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element is essential to the practice of the invention.

As used herein, the term "diabetic" in a Nile rat generally means a random blood glucose>225 mg/dl or fasting blood glucose level of >110 mg/dL.

As used herein, the term "diabetic" in a human generally and currently means a random plasma or blood glucose concentration of $\geq 200$ mg/dL ($\geq 11.1$ mmol/L) or a fasting plasma glucose$\geq 126$ mg/dL ($\geq 7.0$ mmol/L) or a 2 hour post-load glucose$\geq 200$ mg/dL ($\geq 11.1$ mmol/L) during an oral glucose tolerance test.

As used herein, the term "non-diabetic" in a Nile rat generally means a fasting plasma glucose level of $\leq 80$ mg/dL or a random plasma glucose level<200 mg/dL.

As used herein, the term "non-diabetic" in a human generally and currently means a fasting plasma glucose level of <100 mg/dL (5.6 mmol/dL) or a 2 hour post-load glucose<140 mg/dL (<7.8 mmol/dL) during an oral glucose tolerance test.

As used herein, the term "pre-diabetic" in a Nile rat generally means a fasting plasma glucose level of about 80 to about 110 mg/dL.

As used herein, the term "pre-diabetic" in a human generally and currently means a fasting plasma glucose level of 100-125 mg/dL (5.6-6.9 mmol/L) or a 2 hour post-load glucose 140-199 mg/L (7.8-11.1 mmol/L) during an oral glucose tolerance test.

It is appreciated that these definitions are the currently accepted guidelines practitioners generally follow according to the American Diabetes Association (ADA). Guidelines may change over time and vary by region or country and depend upon the group or institution (e.g. ADA, World Health Organization, NIDDK/NIH, CDC, etc.) providing the guidelines, known to those skilled in the art. Physicians may also use clinical experience, the patient's past medical history, and/or other information when deciding on a diagnosis and treatment. These definitions may therefore change over time according to advances in science and medicine.

It will be appreciated that the present invention is also applicable to treating and preventing Latent Autoimmune Diabetes in adults (also known as type 1.5 diabetes).

As used herein, the terms "random" and "nonfasting" generally means at any time during the day or night without regard to time since the last meal.

As used herein, the term "fasting" generally means no caloric intake for at least 12 hours.

As used herein, the term "metabolic imbalance" generally means any disorder or disease state or condition that is associated with an elevated plasma glucose. A metabolic imbalance, for example, comprises diabetes mellitus, gestational diabetes, genetic defects of β-cell function, genetic defects in insulin action, diseases of the exocrine pancreas, endocrinopathies, drug or chemical-induced, infections, other genetic syndromes associated with diabetes, a pre-diabetic state, and metabolic syndrome.

As used herein, the term "nutraceutical" generally means any food that provides an additional benefit other than its nutritional benefit.

Metabolic Syndrome

Metabolic syndrome is characterized by a group of metabolic risk factors in one person, as described by the American Heart Association (AHA). Metabolic syndrome is also known as metabolic syndrome X, syndrome X, insulin resistance syndrome, Reaven's syndrome, or CHAOS. The risk factors include, but are not limited to, abdominal obesity, atherogenic dyslipidemia, hypertension, insulin resistance or glucose intolerance, prothrombotic state (high fibrinogen or plasminogen activator inhibitor-1), and proinflammatory state (elevated C-reactive protein).

Currently, there are no well-accepted criteria for diagnosing the metabolic syndrome. Most commonly used are the National Cholesterol Education Program (NCEP) Adult Treatment Panel III (ATP III). The AHA and the National Heart, Lung, and Blood Institute currently recommend that the metabolic syndrome be identified as the presence of three or more of the following components: elevated waist circumference (males:≧40 inches, females≧35 inches), fasting triglycerides≧150 mg/dL, reduced HDL (males: <40 mg/dL, females<50 mg/dL), blood pressure≧130/85 mm Hg, and fasting glucose≧100 mg/dL. It is appreciated that this is one of many current guidelines practitioners may choose to follow. Guidelines may change over time and vary by region or country and the group or institution (e.g. World Health Organization, NCEP, AHA, etc.) that provide the guidelines.

Nile Rats (*Arvicanthis niloticus*)

Figure 2:
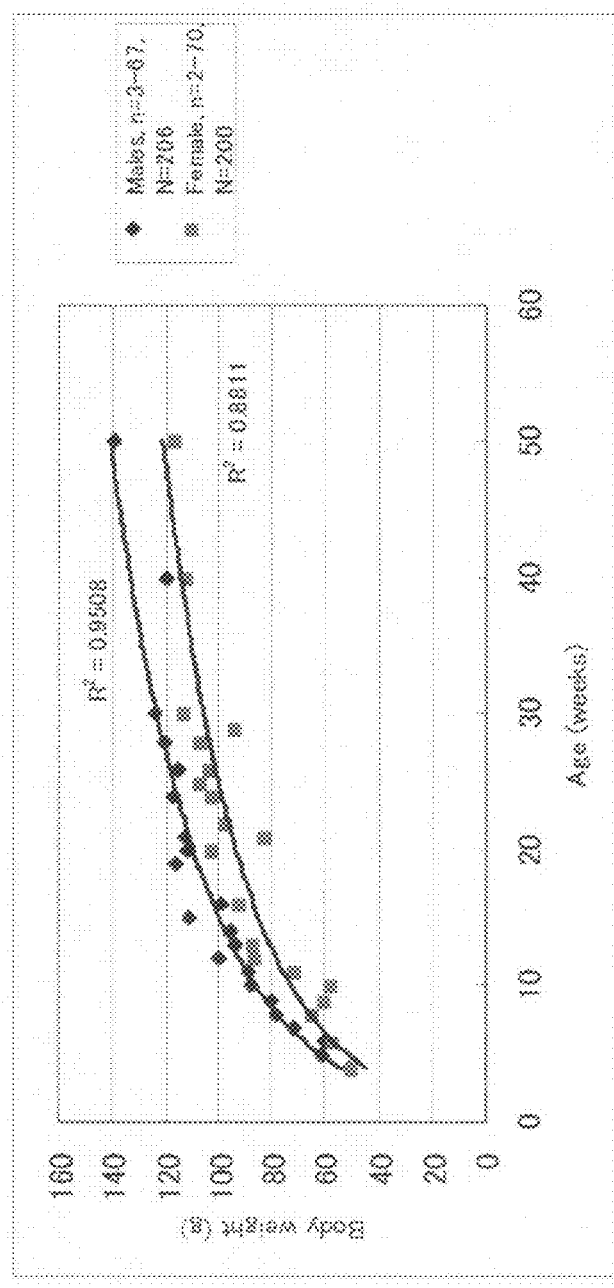
FIG. 2 is a growth graph of male and female Nile rats up to 52 weeks of age.

The Nile rat (FIG. 1), also known as the African grass rat, unstriped grass mouse, or Kuzu rat, is indigenous to the Nile River Delta and parts of the Arabian Peninsula. As used herein, any of these names refer to the animal *Arvicanthis niloticus*. The rodent has coarse, grayish-brown fur. The length of the adult, head and body, is ~13 cm and the tail is another 10 cm. Adult rats weigh 110-130 grams with females being slightly lighter than males (FIG. 2). The growth of non-diabetic female and male Nile rats fed standard rat chow and water is steady and nonlinear between 4 and 30 weeks of age, and plateaus at that point without further growth. Males stabilize at 130-140 g, while females weigh 115-125 g as a final weight. Added weight, as fat, can occur in Nile rats, but is not excessive in most cases. An occasional male may reach 160 g and an occasional female 150 g from added fat. Growth data was collected in male and female rats up to 52 weeks of age fed chow and water. The number of observations at each time point, n, varied between 3 and 67 for males and 2 and 70 for females. The total number of animals surveyed, N, were 206 males and 200 females.

Figure 3:
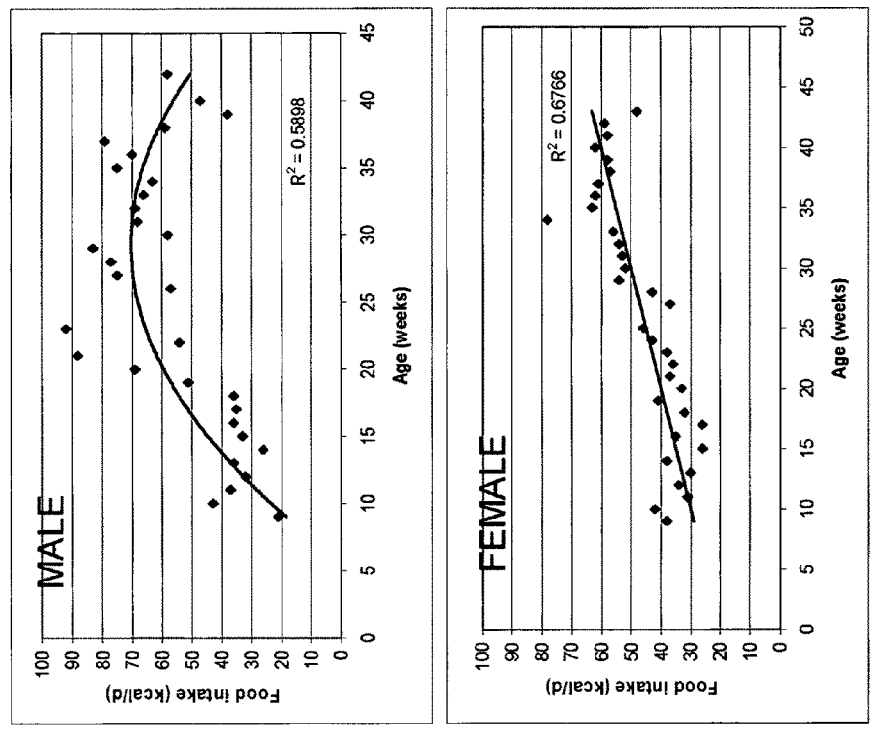
FIG. 3 is a two panel graph showing male and female Nile rat food consumption by age.

The amount of food consumed as lab chow by male and female Nile rats is shown in FIG. 3. Food consumption was measured for 29 female and 19 male Nile rats over 35 weeks. Each time point, n, is represented by 1-12 males and 1-17 females. The female Nile rats displayed a linear relationship with increased food intake over time, while male Nile rats ate less after the 30th week as their glucose intolerance advanced.

Under optimal conditions, Nile rats are able to breed continuously in captivity, with 4-8 pups every 3-4 weeks for 6-12 months. Pups can be weaned at 21 days. From weaning to about 6 weeks old, Nile rats have a fasting glucose of about 40-60 mg/dL. Up to the age of 3-4 months, the blood glucose rises to about 70-80 mg/dL. In captivity, these rats live for about 2 years. Unlike species from the genus *Mus* or *Rattus*, the Nile rat is a diurnal animal, thus being most active during the day. They have been used in studies on circadian rhythm and its regulatory mechanisms.

The laboratory colony of the Nile rats used in the present invention originated from 6 breeding pairs from Laura Smale at Michigan State University (McElhinny, T. L, 1997).

Development of Diabetes in the Nile Rat

In captivity, the Nile rat develops unexpected and spontaneous diabetes with clinical symptoms similar to those found in humans, including a profile with many similarities to metabolic syndrome that is associated with Type 2 diabetes in humans (Lakka, et al., 2002). The disease in Nile rats is characterized by progressive hyperglycemia, hypertriglyceridemia, hyperphagia with polydypsia and polyuria, and ultimately concluding with ketoacidosis, ketonuria, and kidney enlargement followed by terminal nephritis and nephrosclerosis. Insulin sensitivity and secretion fail over time, whereas calorie restriction essentially blocks the appearance of the diabetes, both observations being similar to the human situation. About 10% of Nile rats with advanced diabetes also develop cataracts.

Given standard rat chow (LabDiet, St. Louis, Mo., Formulab Diet #5008 (17% fat, 27% protein)) the Nile grass rat typically consumes 14 g of food (40-50 kcal/day) and drinks roughly 10-20 mL of water per day once mature and free of diabetes. The onset of diabetes in susceptible rats fed chow typically begins to develop as early as 8-12 weeks after birth in many males, and 16-22 weeks for females.

Figure 4:
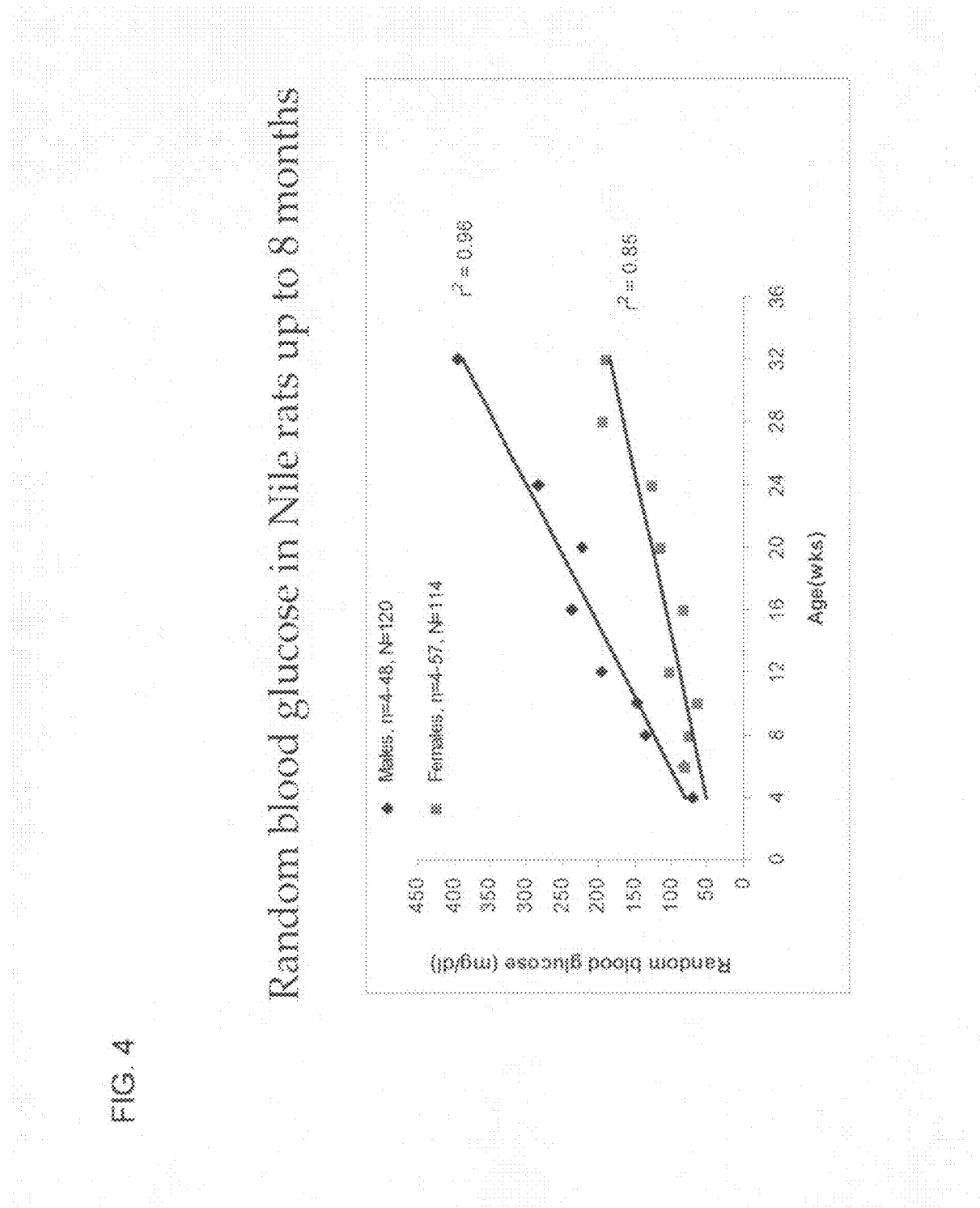
FIG. 4 is a graph of random blood glucose levels in Nile rats up to 8 months of age.

FIG. 4 plots the random blood glucose in male and female Nile rats fed a standard chow and water diet, collected from multiple studies over time. Male rats had higher blood glucose than females at every time point. As early as 8 weeks, males can reach 150 mg/dl and approximately 400 mg/dL by 8 months, with females being somewhat lower. The number of observations at each time point, n, ranged from 4 to 48 in males and 4 to 57 in females. The total number of animals, N, were 120 males and 114 females.

Figure 5:
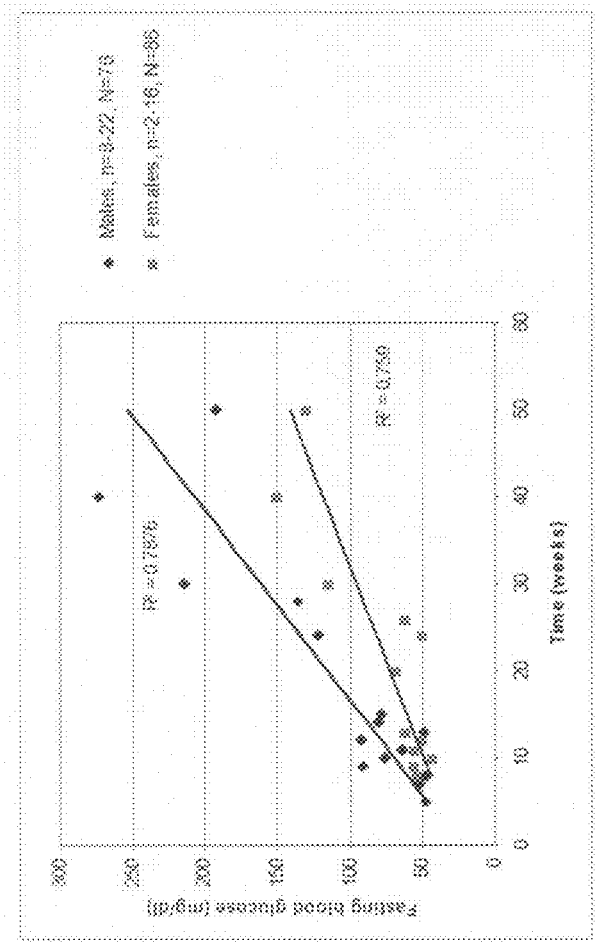
FIG. 5 is a graph of fasting blood glucose levels in Nile rats up to 12 months of age.

FIG. 5 demonstrates the increase in fasting blood glucose in male and female Nile rats on a chow and water diet for 12 months. Fasting blood glucose in males reach 250-300 mg/dL on average, with females at 150 mg/dL. The data in FIG. 5 was compiled from multiple studies. The number of observations at each time point, n, ranged from 8 to 22 in males and 2 to 16 in females. The total number of animals, N, were 76 males and 86 females surveyed.

Figure 6:
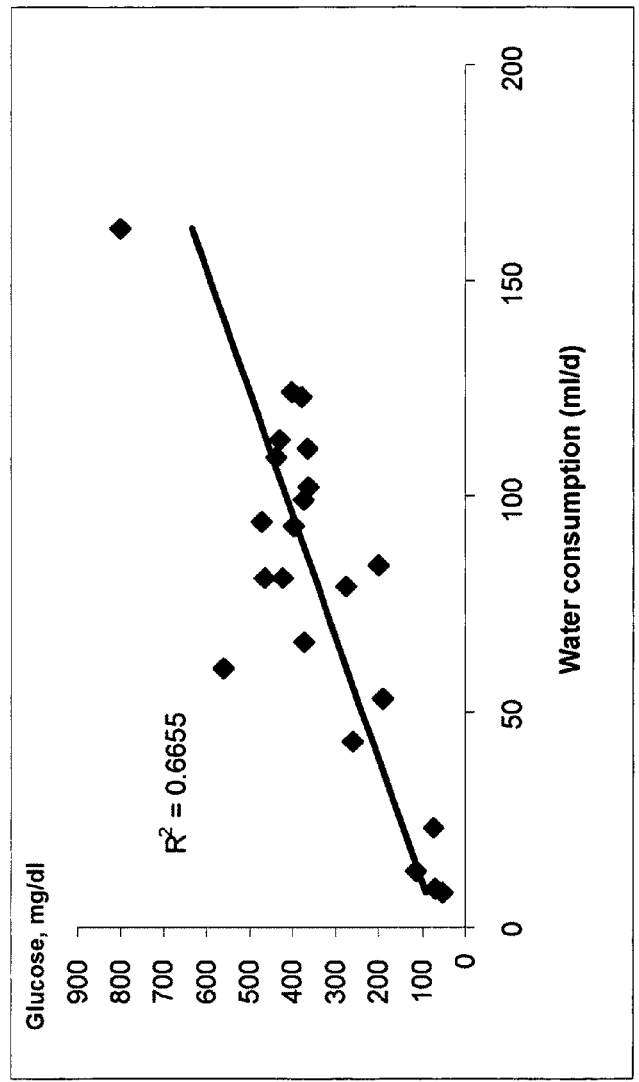
FIG. 6 is a graph of the water intake at different random blood glucose measurements in male Nile rats.

FIG. 6 shows the relationship between random blood glucose and water consumption in male Nile rats between 20 and 32 weeks of age. All animals were given a standard chow diet, and their water intake was measured twice weekly. The results show that the rats exhibited polydipsia, as blood glucose increased, indicating water intake as a means for following the progression of diabetes in this model.

FIGS. 7 and 9 show the food intake (as chow), water intake, and body weight in male Nile rats from age 12 weeks to 40 weeks developing diabetes. These rates demonstrate that food and water intake are associated with a rising blood glucose level. Excess body weight, as fat, is not necessarily a prerequisite to diabetes onset and progression.

FIG. 8 demonstrates that over 90% of males and over 50% of females by the age of 8 months develop diabetes based on blood glucose. The onset of diabetes appears to take place earlier in males than in females. In conjunction with hyperglycemia, these rats exhibit polyuria, polydipsia, and polyphagia. Many rats also develop cataracts, cachexia, diabetic ketoacidosis, and coma by 7-12 months, if left untreated. In addition to developing spontaneous diabetes, Nile rats also exhibit signs and symptoms of the metabolic syndrome, which is characterized by a group of metabolic risk factors as described previously.

Methods for studying diabetes include measurement of physiological changes and analysis of blood or plasma. These include, but are not limited to, growth dynamics, body mass index (BMI), lean mass index (LMI), food and water intake, sex differences, fasting and random blood glucose, triglycerides (TG), lipoproteins, cholesterol, liver weight and liver lipids, kidney size and function, a glucose tolerance test (GTT), insulin tolerance test (ITT), blood insulin concentration, pancreatic islet cell morphology, high-fat diets, and caloric restriction.

Figure 10:
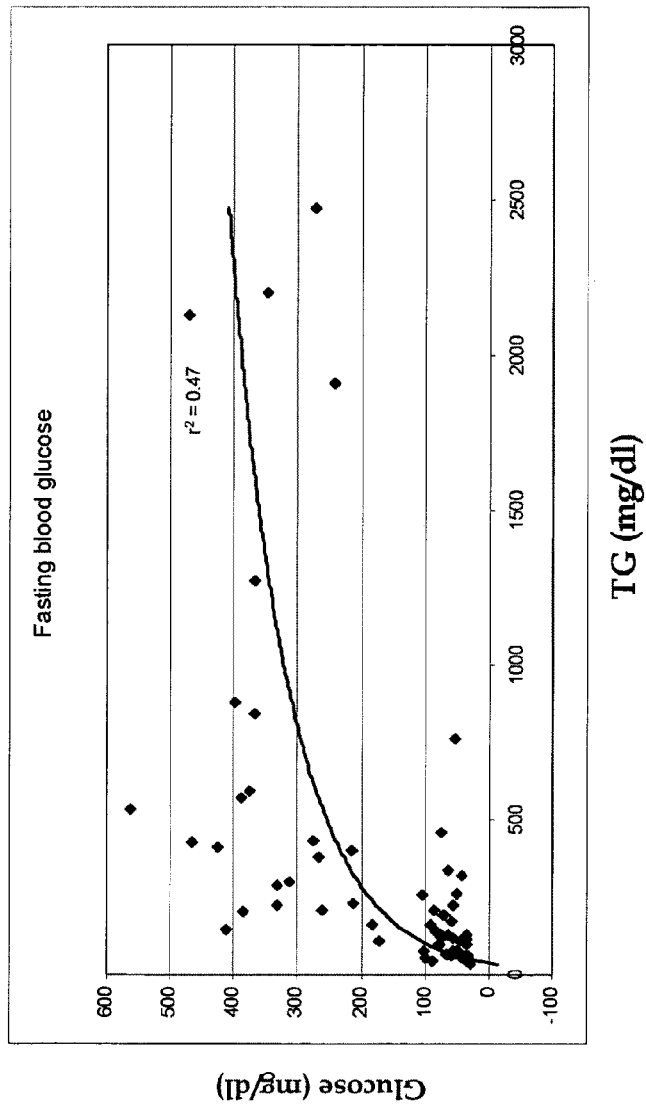
FIG. 10 is a graph of the fasting blood glucose levels versus triglyceride levels in Nile rats.
Figure 11:
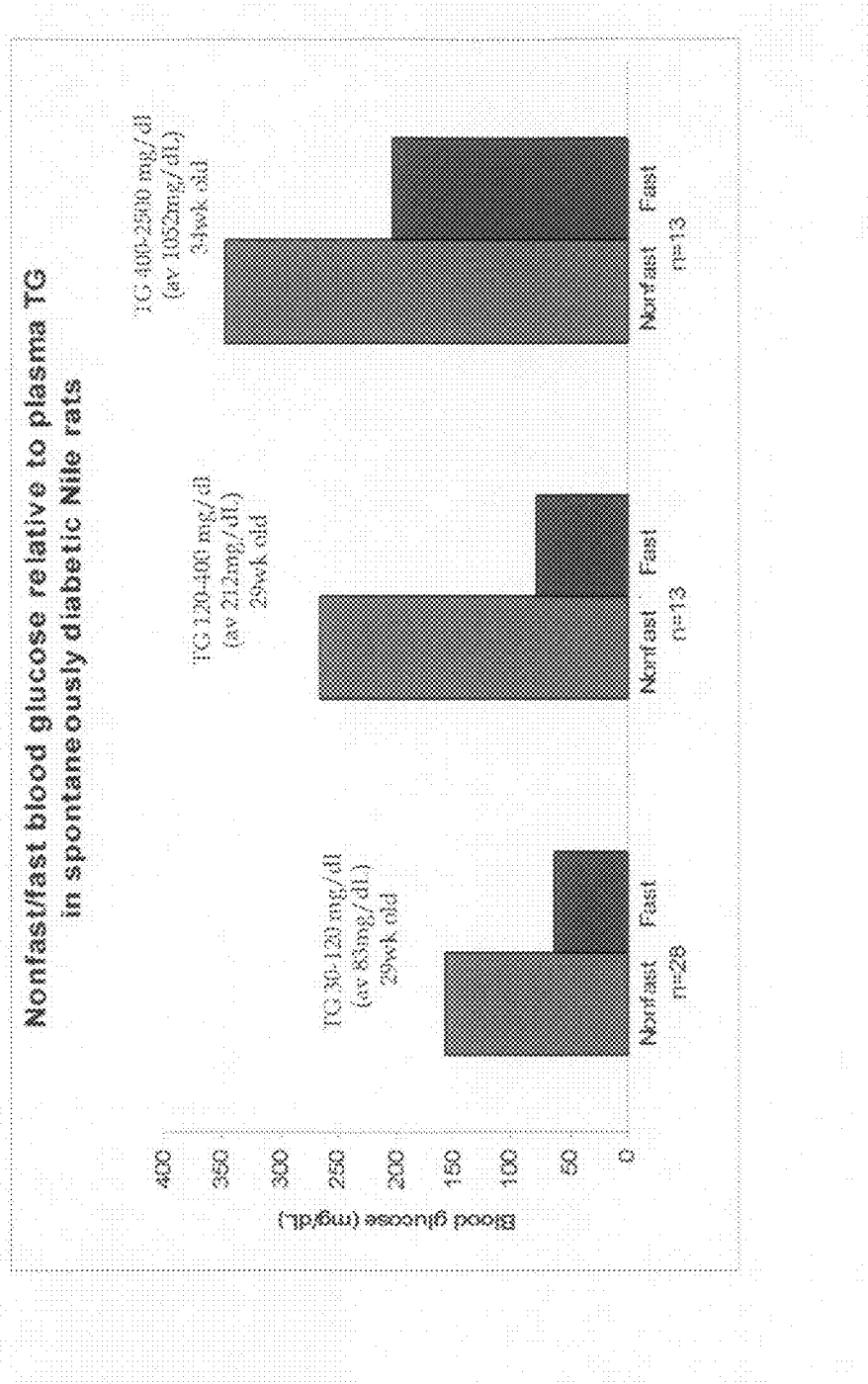
FIG. 11 is a graph of the nonfasting or fasting blood glucose level in relation to triglyceride level in spontaneously diabetic Nile rats.

Diabetic Nile rats often develop hypertriglyceridemia. When fasting blood glucose was compared to fasting triglyceride levels (FIG. 10), a TG level>125 mg/dL was often associated with elevated blood glucose. FIG. 11 shows that animals with low random and fasting blood glucose typically have lower triglycerides compared to those within the higher ranges of blood glucose. The data indicate that a combination of an elevated fasting glucose plus a high triglyceride level (i.e. a fasting triglyceride>125 mg/dL) is the best indicator of diabetes. The majority of the animals in the low triglyceride group were females, as opposed to the male majority in high triglyceride group. Male and female rats were evenly distributed among categories in the intermediate triglyceride group.

Diabetic Nile rats often exhibit severely elevated lipoproteins (FIG. 12). In association with the hyperglycemia, a marked increase was seen in very low-density lipoprotein (VLDL), low density lipoprotein (LDL), triglycerides (TG), and total cholesterol (TC). At the time of this study, 18 Nile rats of mixed gender were divided into three groups depending on their fasting blood glucose: nondiabetic, below 60 mg/dl; prediabetic, 61-150 mg/dl; diabetic, above 150 mg/dl. Lipoproteins were isolated following ultracentrifugation of plasma. TG, TC, VLDL-C and LDL-C were all found to be significantly increased in diabetic rats compared to non-diabetic and pre-diabetic animals, which tended to have similar lipid profiles. Little difference was seen in the percent of LDL-C between groups, but HDL-C was approximately ten times greater in non-diabetic and pre-diabetic animals (50% and 67%, respectively) compared to diabetic Nile rats (6%). However, no significant difference was observed between absolute values of HDL-C, though it tended to be depressed in diabetics. The LDL-C/HDL-C ratio appeared higher in the diabetic animals, but the variance within groups precluded the difference from reaching significance. By contrast, the TC/HDL-C ratio was approximately ten times greater in the diabetic group compared to the non-diabetic and pre-diabetic groups ($p<0.05$) due to the excessive amount of VLDL-C.

Figure 13:
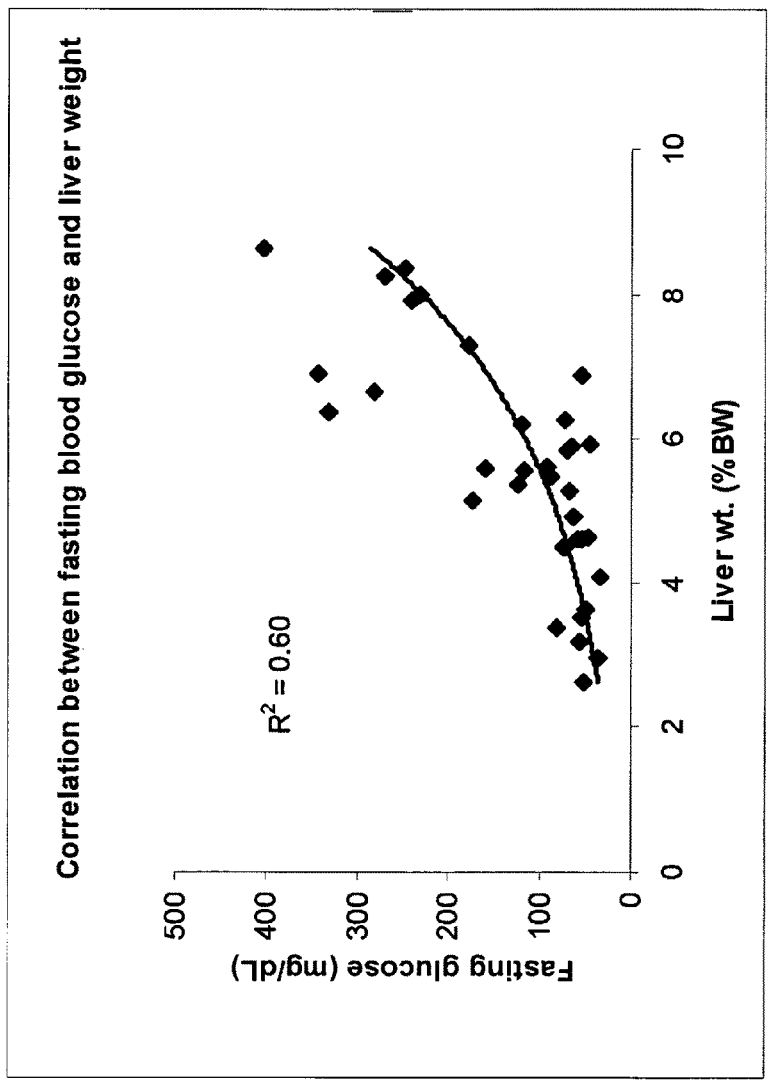
FIG. 13 is a graph of fasting blood glucose level and liver weight.

A positive correlation between liver weight and fasting blood glucose was found in a study that examined the effect of diet fat on diabetes (FIG. 13). A greater liver weight was more indicative of elevated fasting blood glucose and vice versa. The increased liver weight was associated with liver TG accumulation in some, but not all, studies.

Nile rats (7-5 week old males and females) were divided into four groups based on fasting blood glucose, and their fasting insulin concentrations determined (FIG. 14). In general, insulin tended to increase as diabetes developed and glucose rose above 100 mg/dL. Fasting blood glucose>150 mg/dL was linked with insulin resistance initially, and the insulin concentration eventually decreased in animals with an abnormally high blood glucose. This suggests β-cell exhaustion and reduced insulin secretion as diabetes advanced. The large standard deviation for insulin, however, demonstrates the variation within each group.

The varied insulin response to glucose challenge was quantified in Nile rats subjected to a an intraperitoneal (IP) glucose tolerance test (FIG. 15). Measurements were taken at 0 and 60 minutes post-injection from tail bleeds using an Elite XL Glucometer. Insulin concentration was measured by ELISA assay based on antibody for rat insulin. In general, these rats reacted in a manner consistent with insulin resistance and impaired insulin secretion. For example, animal 206M had a nine-fold increase in insulin at 60 min, yet blood glucose remained elevated at 491 mg/dL, indicating insulin resistance. A defect in insulin secretion already was apparent in animal 97M where the initial blood glucose was 454 mg/dL, increasing further to 738 mg/dL because insulin increased insufficiently by only 0.6 ng/mL. Healthy rats, such as m58M had an initial fasting glucose of 40 mg/dL and only rose to 89 mg/dL with a minimal insulin rise. Rat 114M needed a 5-fold increase in insulin to maintain a relatively low blood glucose of only 90 mg/dL at 60 min, suggesting a possible early stage of insulin resistance.

Figure 16:
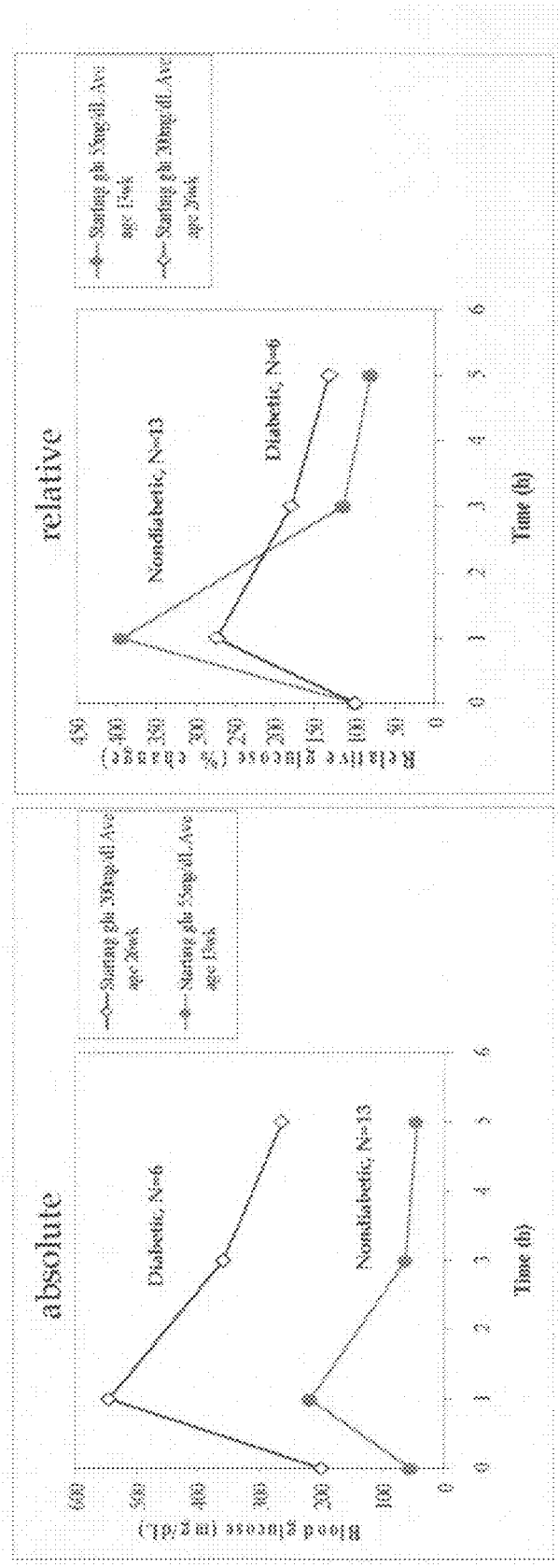
FIG. 16 is a panel of two graphs showing the absolute and relative response to an intraperitoneal glucose tolerance test in diabetic and nondiabetic Nile rats.

Glucose tolerance testing was also conducted on 19 male Nile rats (6 diabetics, 13 normal) between the ages of 5 and 47 weeks old (FIG. 16). All animals were fasted 15 hours overnight and injected with 2.5 g/kg body weight glucose solution. Blood glucose was then measured at 0, 1, 3 and 5 hours post-injection from tail bleeds using an Elite XL Glucometer. Rats were grouped as diabetic or non-diabetic depending on their response. The diabetic group started with a fasting blood glucose of 200 mg/dL and peaked after one hour at 550 mg/dL. After five hours, the blood glucose of these diabetic animals was still above the initial value. The non-diabetic group had an initial fasting blood glucose of only 55 mg/dL and peaked after 1 hour at 200 mg/dL. In just 3 hours, the blood glucose returned to the initial value, and after 5 hours it had decreased to 44 mg/dL. The relative response (% change) demonstrates that the non-diabetic rats reacted more dynamically to the glucose dose compared to their diabetic counterparts, rising sharply, but returning rapidly to their initial, normal blood glucose level.

An insulin tolerance test (ITT) (FIG. 17) demonstrates the absolute and relative glucose response to intraperitoneal insulin injected in non-fasting Nile rats categorized as diabetic or nondiabetic, based on their blood glucose. These 8 diabetic and 7 non-diabetic Nile rats (9 to 55 weeks of age) had been fed chow and water. They were given an IP injection of insulin at 0.5 IU/kg body weight. Blood glucose was measured 15 minutes after the injection and then at 30 minute intervals from tail bleeds using an Elite XL Glucometer. The blood glucose bottomed at 60 minutes in non diabetic rats, and after 120 minutes had almost fully recovered from the insulin dose. By contrast, the blood glucose in the diabetic group decreased slowly and minimally, even 120 minutes post-injection. This suggests insulin resistance in the diabetic animals, with glucose levels remaining high even in the presence of elevated insulin levels.

The relative glucose response (FIG. 17) clearly demonstrates the physiological mechanisms at play. The blood glucose level in the non-diabetic rats decreased rapidly after insulin injection, beginning glucose recovery after 60 minutes. On the other hand, the diabetic group failed to respond normally, displaying a sluggish decrease in blood glucose that continued up to 120 minutes post-injection.

Eight 40 week old female Nile rats were selected as early to pre-diabetic based on fasting blood glucose (average=117 mg/dL) and then fed diets with different levels of fat for 12 weeks, at which time the fasting blood glucose was 223 mg/dL in the high-fat diet group, but had reduced to 82 mg/dL in the low-fat group (p<0.05). At termination, their body weight, carcass weight, and length were measured and used to calculate BMI and LMI to examine these indices of obesity for possible association with diabetes status. BMI was calculated by dividing the body weight in kilograms by the length in meters squared, with length measured from the nose to the tail base. LMI was calculated in the same way, except the carcass weight (after removal of all organs and body fat pools) was used instead of total body weight. The data (FIG. 18) reveal marked differences in diabetes (blood glucose), even though BMI and LMI were comparable between groups. In other words, the presence or absence of obesity was not a prerequisite for developing diabetes in this model, and no relationship was found between the BMI or LMI and blood glucose differences, either as a function of diets or associated with change in blood glucose over the 12 weeks. This also indicates that improvement in diabetic status of the Nile rat (i.e. shifting from pre-diabetes to normal (non-diabetic) by diet manipulation) can proceed without inducing differences in body mass or lean mass.

Figure 22:
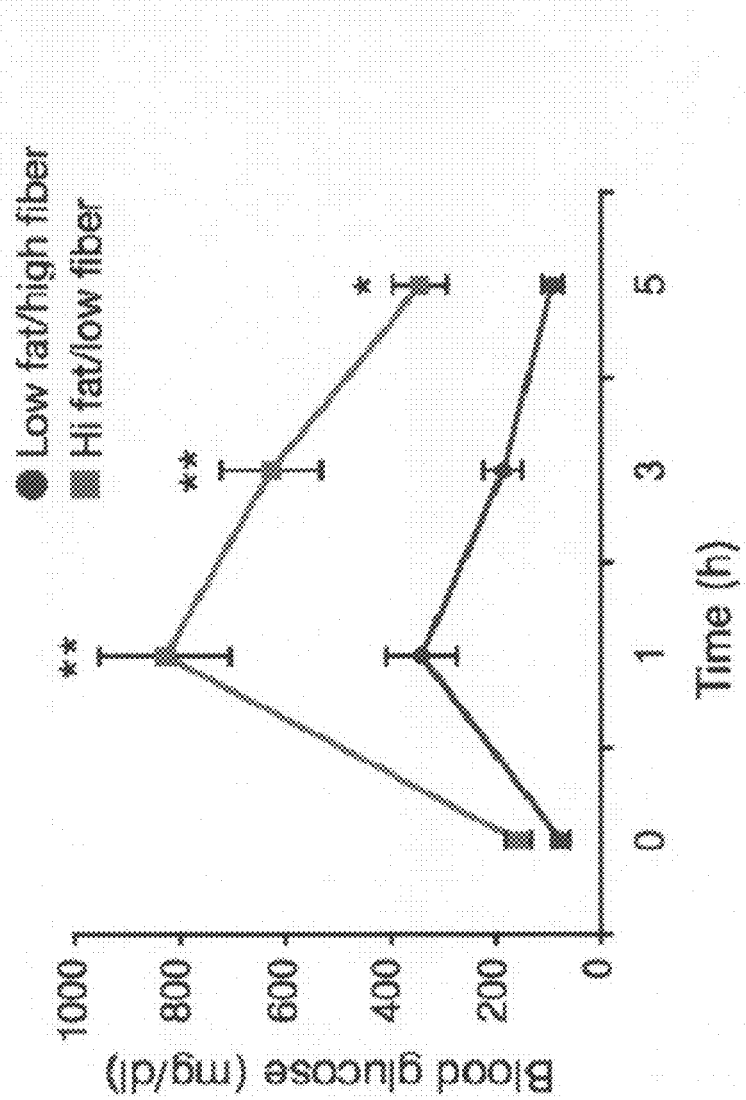
FIG. 22 is a graph of a glucose tolerance test in Nile rats fed 3 different diets.
Figure 23:
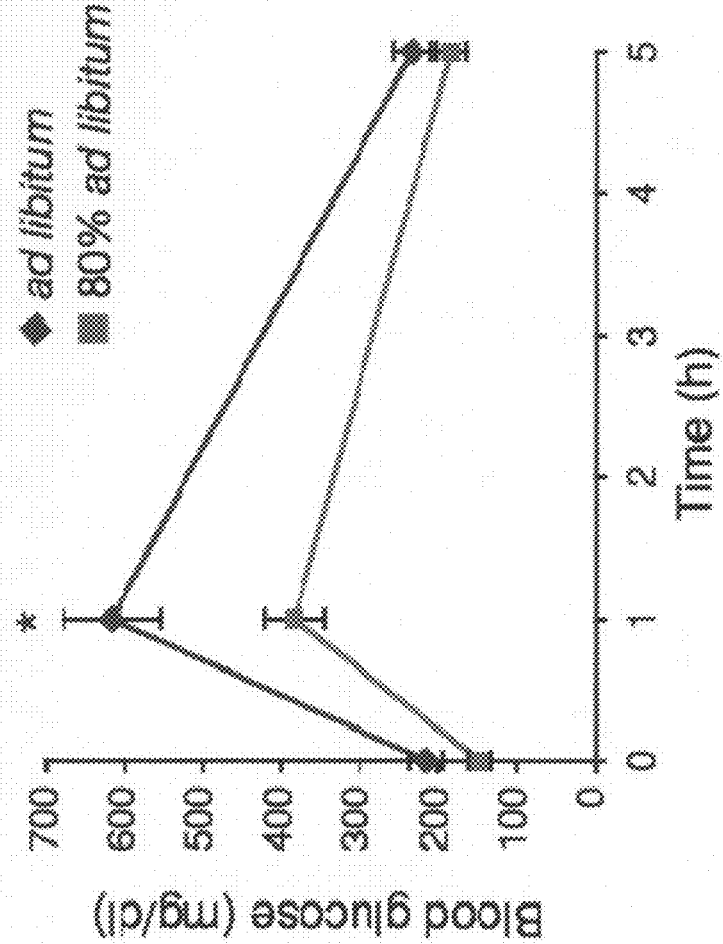
FIG. 23 is a graph of an intraperitoneal glucose tolerance test in male Nile rats fed rat chow ad lib or 80% ad lib intake.
Figure 24:
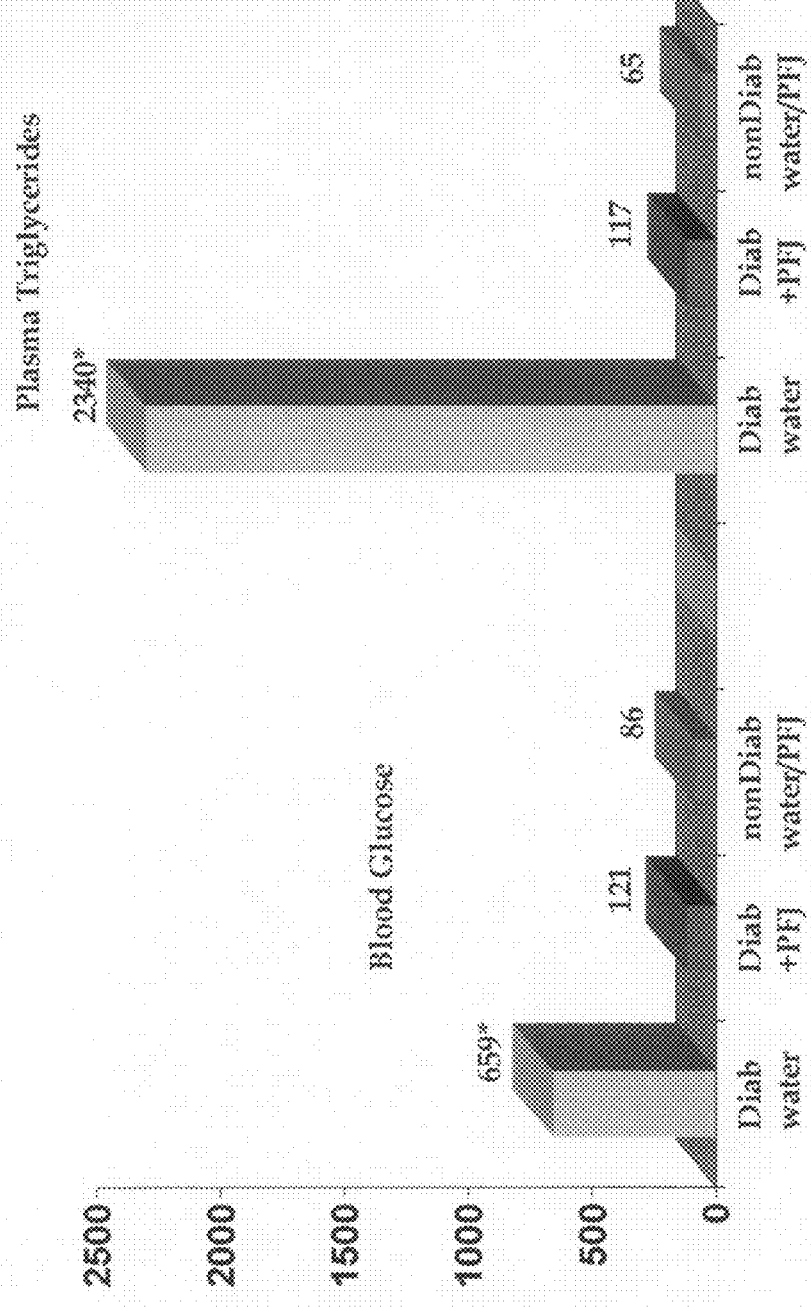
FIG. 24 is a bar graph of blood glucose and plasma triglyceride levels in diabetic and nondiabetic Nile rats fed either water or palm fruit juice.
Figure 25:
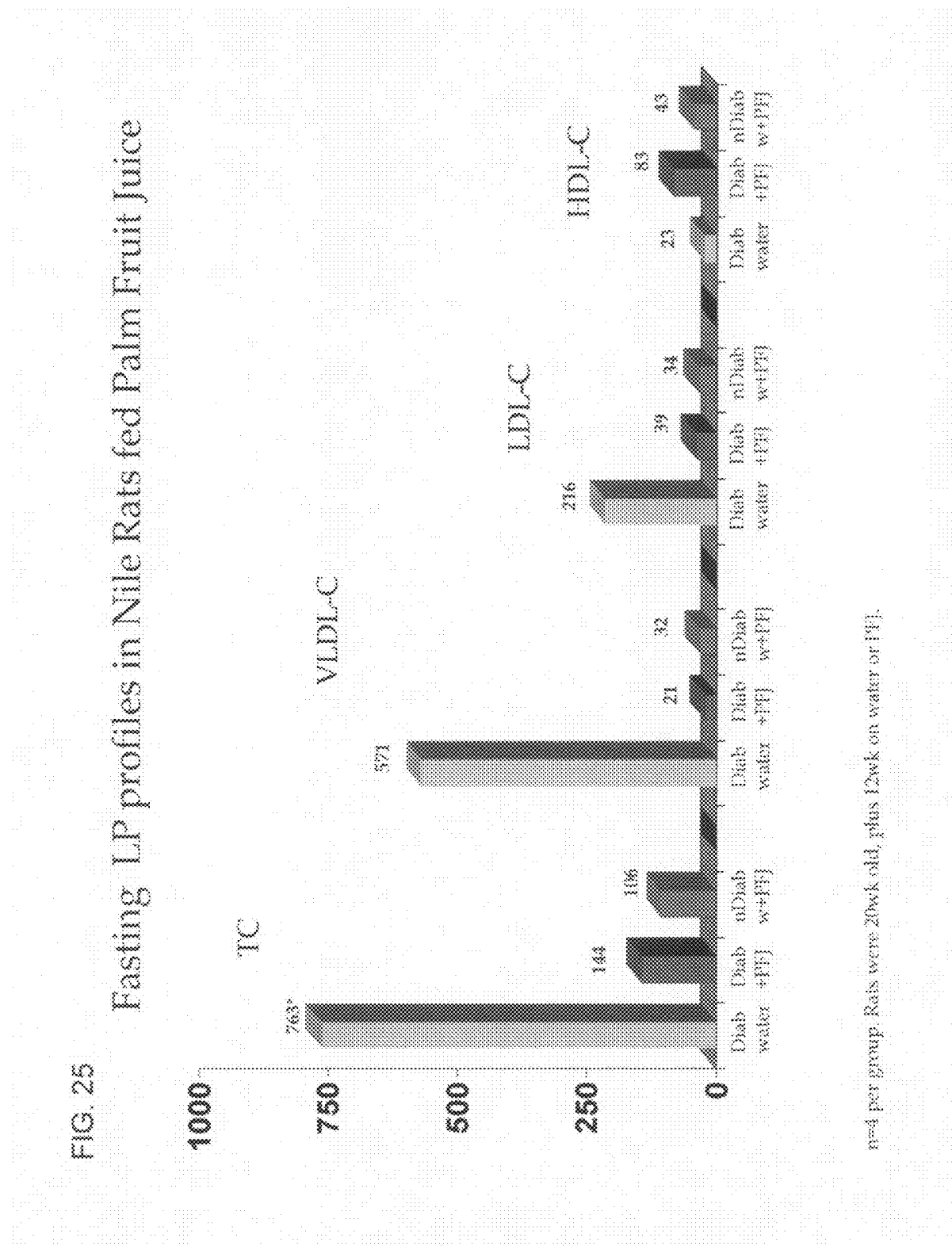
FIG. 25 is a bar graph of fasting lipoprotein profiles in Nile rats fed palm fruit juice or water.
Figure 26:
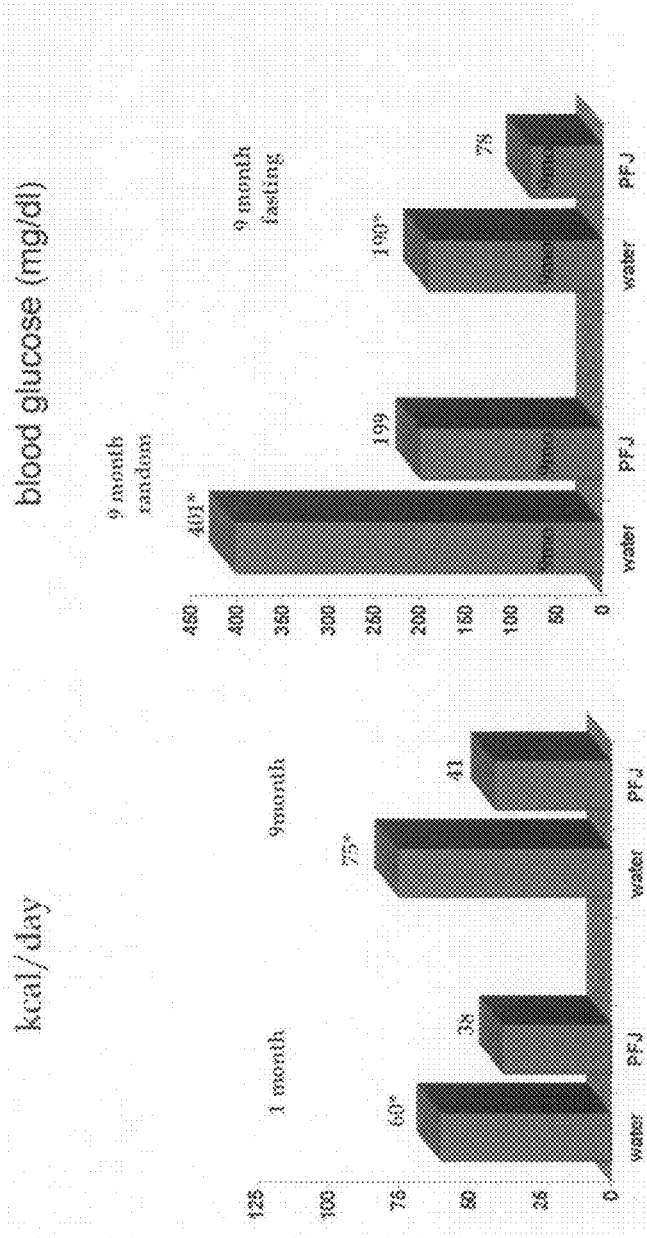
FIG. 26 is a bar graph of the food intake and blood glucose levels in 3 month old Nile rats fed either water or palm fruit juice after 1 month and 9 months.
Figure 27:
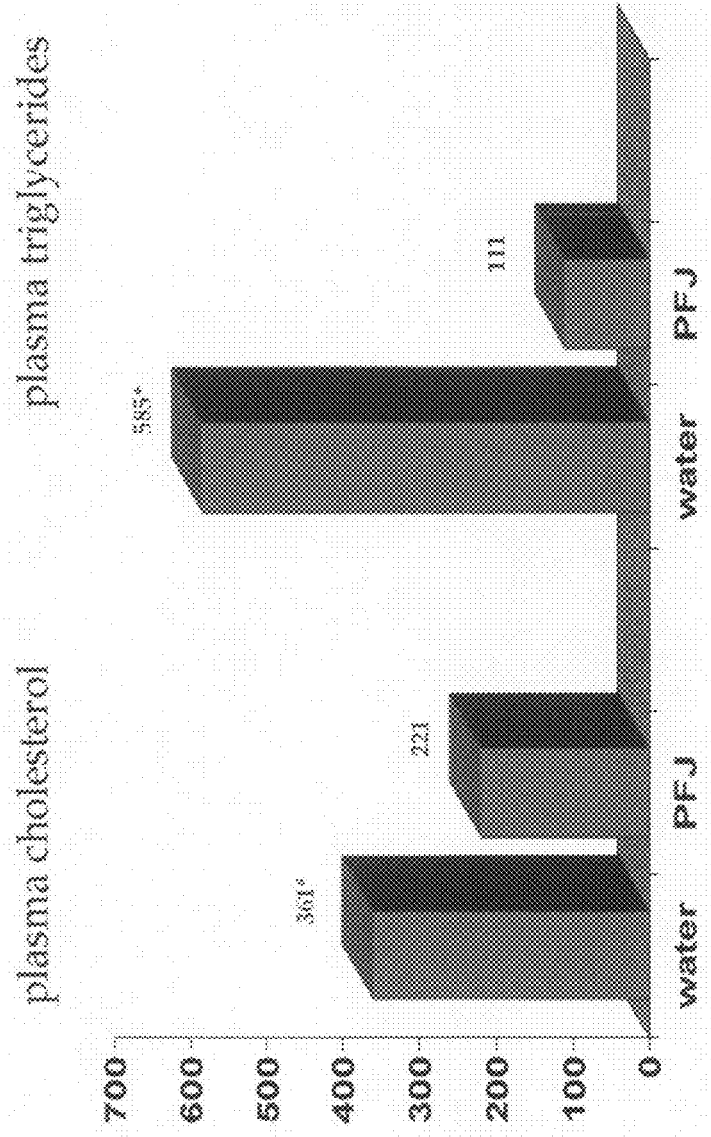
FIG. 27 is a bar graph of plasma lipids in 3 month old Nile rats given water or palm fruit juice for 9 months.
Figure 28:
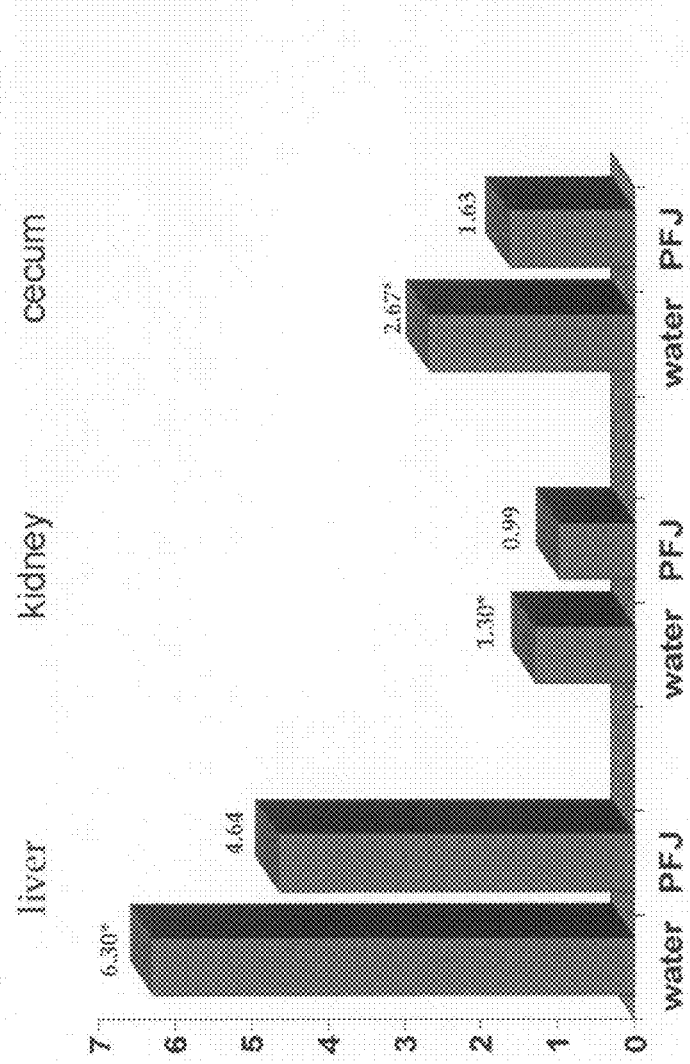
FIG. 28 is a bar graph of the organ weights (% body weight) in 3 month old Nile rats given water or palm fruit juice for 9 months.

In another study, 15 weanling male Nile rats were fed one of three diets for 5 months (n=5/group): low-fat/high-fiber, high-fat/low-fiber, or CHOW #5008 (FIGS. 19-22). Body weight did not differ significantly for any diet group, although the low-fat diet rats tended to gain the least amount. The rats fed the low-fat diet also had the lowest terminal fasting glucose (FIG. 19). Significant increases were seen in the plasma total cholesterol and triglyceride levels, as well as liver lipids in the high-fat, low-fiber group (FIG. 20). Hepatomegaly and nephromegaly also were seen at the end of the 5 month period in the high-fat, low-fiber diet group (FIG. 21). Nile rats on the high fat/low fiber diet also exhibited the least control over blood glucose after an intraperitoneal glucose tolerance test (ipGTT) at the end of the 5 month period (FIG. 22). This indicated that high-fat diet induced several aspects of the Metabolic Syndrome and diabetes compared to the other two diets.

Other Dietary Manipulations

As indicated from the above, Nile rats, particularly males, are suitable for experimentation related to nutritional manipulations. The animals can be fed for many months with purified diets made in-house without detrimental health effects.

Calorie Restriction

The effect of calorie restriction on diabetes status was studied in mature Nile rats, the first study with diabetic rats and the second prior to diabetes onset. In the first, male Nile rats 32 wk old (fasting blood glucose about 300 mg/dl) were fed either ad lib lab chow or 80% of the caloric intake of the ad lib group. Even though neither group changed body weight during the 14 wk study and had essentially the same final body weights (about 120 g average), the fasting blood glucose improved significantly for the restricted group (to about 150 mg/dl) after 14 wk with controls at slightly over 200 mg/dl. A glucose tolerance test at the end of the study supported the positive effect of calorie restriction on blood glucose, with the restricted group demonstrating much better glucose control.

A second restriction study ran 18 wks and included a group of eleven 20-week old nondiabetics (6 males and 5 females), with six animals fed a restricted chow diet (at 75% of the ad lib group) for the 18 weeks. At the time of sacrifice, the fasting blood glucose for the ad lib group had increased from an initial 56 mg/dl to 211 mg/dl while the restricted saw only a minor increase from 60 mg/dl to 72 mg/dl from beginning to end of the study. Comparison of these terminal glucose values between groups was statistically significant. During an ipGTT the restricted group rose from 72 mg/d to 226 mg/dl at 1 hour, while the ad lib glucose rose from 211 mg/dl to 517 mg/dl, almost twice that of the restricted group. Five hours after glucose injection the ad lib and restricted groups had blood glucose of 233 mg/dl and 184 mg/dl, respectively, suggesting that insulin resistance in the ad lib group was worse than that in the restricted group. The liver was significantly lighter (25%, p<0.05) in the restricted group compared to the ad lib controls.

The results from these two studies indicate that restricting calories from a chow diet in older Nile rats has a beneficial effect on the fasting blood glucose, even though mild restriction did not depress body weight. Similarly, caloric reduction and weight loss in humans typically improve insulin tolerance in patients with type 2 diabetes (Aucott, et al., 2004).

The Oil Palm (*Elaeis*)

The oil palms comprise two species of the Arecaceae (palm) family, *Elaeis guineensis* (native to West Africa) and *Elaeis oleifera* (native to Central and South America). Most commonly used in commercial agriculture in the production of palm oil, mature trees grow to 20 m tall. The fruit takes five to six months to mature from pollination and comprises an oily, fleshy outer layer (pericarp) with a single seed (kernel). The oil palm does not produce offshoots and propagation is by sowing seeds. A cluster of fruit can weigh 40-50 kg.

The African Oil Palm was introduced into Sumatra and Malaysia in the early 1900s. The majority of world production now comes from Malaysia. Studies have shown various uses of the oil palm and its fruit, which provides both edible oil and a water-soluble extract (Abeywardena et al. (Asia Pacific J Clin Nutr, 2002), Tan et al. (Eur J Lipid Sci Technol, 2007), Zunino et al. (J Nutr, 2007), and Hayes and Khosla (Eur J Lipid Sci Technol, 2007)) which are hereby incorporated by reference. Palm fruit juice has been used in African recipes, such as Palm Butter Soup. Palm-butter is made from the fruit, which also contains the red palm oil which can be further refined. If you live outside the tropics and cannot obtain fresh palm nuts, canned palm soup base or palm nut pulp (also called sauce graine, noix de palme, or cream of palm fruit) is the same thing and can be used in recipes, including the recipe below. Canned Palm Soup Base may be found in International or African grocery stores. A basic Palm Butter Sauce may be made by using approximately one hundred fresh, ripe, palm nuts (available only in the tropics). The recipe is as follows: (1) Bring two or three cups of water to a boil in a saucepan; (2) Place the palm nuts in the boiling water (they do not need to be covered by the water); (3) Cover and cook the palm nuts for a few minutes, until the skins begin to come off; (4) Drain the water from the pan and use a potato masher (or a mortar and pestle) to crush the palm nuts into a pulp; (5) Combine the palm nut pulp with one to two quarts (or liters) of cold water; Stir; and Squeeze the palm nuts with your hands to remove all the fruit and oil from the palm nuts; (6) Press the pulp through a strainer into the saucepan (rinse it first); (7) Discard the nut skins and kernels that remain in the strainer; (8) Strain it twice, to remove all the nut kernels and bits of skin, and to make sure all the oil and fruit end up in the saucepan; (9) Heat the pulp to a low boil, stir often, and cook until the sauce is thickened (approximately an hour); and (10) Once the sauce is heated, other ingredients can be added. Palm butter may be made in large quantities and may be frozen for use later.

Other studies have shown the anti-diabetic effects of extracts and juices from other natural plant sources including, for example, Xie et al. (J Food Sci, 2007), Attele (Diabetes, 2002), El-Alfy et al. (Pharma Res, 2005), Aviram et al. (Am J Clin Nutr, 2000), Wu et al. (Eur J Nutr, 2004), Zunino et al. (J Nutr, 2007), and Singh et al. (Clinical Chimeica Acta, 2005), and are hereby incorporated by reference.

The water-soluble extract of the vegetation liquor from the palm oil milling process (referred to here as palm fruit juice) comprises phenolics that are believed to possess anti-diabetic and anti-hyperglycemic properties. The phenolics found in palm fruit juice comprises, but is not limited to cinnamate and benzoate derivatives such as vanillic acid, chlorogenic acid, catechin, caffeic acid, protocatechuic acid, gentisic acid, 4-hydroxybenzoate, coumaric acid, ferulic acid, and rutin hydrate.

In general, the methods encompass any dosing regimen that is efficacious in treating or preventing diabetes. In certain embodiments, the source of palm fruit juice is given to a patient in a single dose or multiple doses. The single dose may be administered daily, or multiple times a day, or multiple times a week, or monthly, or multiple times a month. In certain embodiments, the source of palm fruit juice is given in a series of doses. The series of doses may be administered daily, or multiple times a day, weekly, or multiple times a week, or monthly, or multiple times a month.

The palm fruit juice-containing formula may be administered for therapy to a patient in any conventional manner. While it is possible for the palm fruit juice-containing formula to be administered as the raw liquid, it may also be presented as a nutritional fruit juice or as a pharmaceutical formulation. Natural drinks or pharmaceutical formulations according to the present invention comprise the palm fruit juice-containing complex alone or a pharmaceutically acceptable salt thereof, together with one or more pharmaceutically acceptable carriers or excipients and optionally other therapeutic agents. The carrier(s) must be acceptable in the sense of being compatible with the other ingredients of the formula and not deleterious to the recipient thereof. When the individual components of the combination are administered separately, they may be presented as a nutraceutical and/or pharmaceutical formulation.

The nutraceutical or pharmaceutical formulations of the invention may include one or more other medicinal agents, pharmaceutical agents, carriers, adjuvants, and/or diluents. For example, a source of palm fruit juice may be combined with other active agents for the treatment of diabetes and other diseases and/or disorders described herein. Suitable oral antidiabetic agents include sulfonylureas, meglitinides, biguanides, thiazolidinediones, and α-glucosidase inhibitors.

Examples of carriers or recipients for oral administration include cornstarch, lactose, magnesium stearate, microcrystalline cellulose and stearic acid, povidone, dibasic calcium phosphate and sodium starch glycolate. Any carrier suitable for the desired administration route is contemplated by the present invention.

The compositions of the present invention may be contained in a solid dosage form (e.g., a pill, capsule, or tablet), a semi-solid dosage form or a liquid dosage form, each containing a predetermined amount of active ingredient. In certain embodiments, a solid dosage form is coated for ease of swallowing. The compositions of the present invention may be in the form of a powder or granules; or as a solution or suspension. For oral administration, fine powders or granules may contain diluting, dispersing, and or surface active agents and may be present in a solution or suspension in water or syrup, capsules or sachets in the dry state, in a nonaqueous solution or suspension wherein suspending agents may be included, or in tablets wherein binders and lubricants may be included. Components may be added such as flavoring, preservative, suspending, thickening or emulsifying agents.

Oral delivery methods are often limited by chemical and physical barriers imposed by the body, such as the varying pH in the gastrointestinal tract, exposure to enzymes, and the impermeability of the gastrointestinal membranes. Methods of the present invention for orally administering the nutritional supplement or pharmaceutical formulation may also include the co-administration of adjuvants with the compositions of the present invention. For example, nonionic surfactants such as polyoxyethylene oleyl ether and n-hexadecyl polyethylene ether can be administered with or incorporated into the formulations of the present invention to increase artificially the permeability of the intestinal walls. Other methods include the co-administration of enzymatic inhibitors with the formulations of the present invention. The active ingredients may also be present as a bolus or paste or may be contained within liposomes and emulsions.

Formulations for rectal administration may be presented as a suppository or enema.

When administered in the form of an aqueous liquid solution, the formulation will contain the source of palm fruit juice and water. Optional components in liquid solution include suitable solvents, buffering agents, sweeteners, antimicrobial preservatives, flavoring agents, other fruit juices, and mixtures thereof. A component of the formulation may serve more than one function. For example, a suitable buffering agent may also act as a flavoring agent as well as a sweetener.

Suitable solvents in the liquid solution used in the present invention include, for example, sorbitol, glycerin, propylene glycol, and water. A mixture of two or more solvents may optionally be used. The solvent or solvent system is typically present in an amount of from about 1% to about 90% by weight of the total liquid formulation.

Suitable buffering agents include, for example, citric acid, sodium citrate, phosphoric acid, potassium phosphate, and various other acids and salts. A mixture of two or more buffering agents may optionally be used. The buffering agent or mixtures thereof are typically present in an amount of from about 0.001 wt. % to about 4 wt. %.

Suitable sweeteners include, for example, saccharin sodium, sucrose, and mannitol. A mixture of two or more sweeteners may optionally be used. The sweetener or mixtures thereof are typically present in an amount of from about 0.001 wt. % to about 70 wt. %.

Suitable anti-microbial preservatives include, for example, methylparaben, propylparaben, sodium benzoate, and benzalkonium chloride. A mixture of two or more preservatives may optionally be used. The preservative or mixtures thereof are typically present in an amount of from about 0.0001 wt. % to about 2 wt. %.

Suitable flavoring agents may be used to the liquid solution a cherry flavor, cotton candy flavor, or other suitable flavor to make the solution easier for a patient to ingest. The flavoring agent or mixtures thereof are typically present in an amount of from about 0.0001 wt. % to about 5 wt. %.

Nutraceutical Formulations

The present invention provides a natural food formulation made from fruit extracts of *Elaeis*. The present invention provides an extract that can be presented in a powdered, liquid, or solid form. The present section discusses the forms and components of formulations that would be desirable and readily produced given the teachings of the present invention.

The extract is likely a reconstitutable concentrate or powder composition that, when reconstituted with, for example, water, milk, fruit juice or some other similar liquid will provide a drink, which may be used to provide an anti-hyperglycemic activity to a subject in need thereof. The concentrate or powdered composition and drink prepared therefrom are especially useful as an enterally administered component in a program of diabetes management which utilizes a number of carefully designed products in various forms, i.e., in shake, soup, fruit drink, snack bar and other solid forms such as tablets, gel caps, and the like, which can be mixed and matched over a period to provide more attractive and, therefore, more effective support to a patient, particularly those in extended care situations.

In addition to drinks, the extracts of the present invention may be used in foodstuffs. Such extracts may be combined with any other foodstuff, for example, water-soluble foodstuffs containing the extracts of this invention may be used. Grain flour fortified with the compounds of this invention may be used in foodstuffs, such as baked goods, cereals, pastas and soups. Advantageously, such foodstuffs may be included in low fat, low cholesterol or otherwise restricted dietary regimens.

Nutraceuticals may include nutritional drinks, diet drinks as well as sports herbal and other fortified beverages. The present invention provides nutraceutical compositions that may be used as an anti-diabetic agent. As such, it can be used to relieve any metabolic condition or imbalance that results in elevated blood glucose including but not limited to, diabetes mellitus, gestational diabetes, genetic defects of β-cell function, genetic defects of insulin action, diseases of the exocrine pancreas, endocrinopathies, drug or chemical-induced, infections, other genetic syndromes associated with diabetes, a pre-diabetic state, metabolic syndrome and the like.

In addition to the purified extract, the nutraceutical or foodstuff also may contain a variety of other beneficial components including but not limited to essential fatty acids, vitamins and minerals. These components should be well known to those of skill in the art, however, without being bound to any particularly formulations or content the present section provides a brief discussion of components that could form part of the food supplements of the present invention. Additional disclosure describing the contents and production of nutritional supplements may be found in e.g., U.S. Pat. Nos. 5,902,797; 5,834,048; 5,817,350; 5,792,461; 5,707,657 and U.S. Pat. No. 5,656,312 (each incorporated herein by reference). Essential fatty acids such as γ-linolenic acid (ω-3) and linoleic acid (ω-6) may be added to the food supplements of the present invention. Essential fatty acids are involved in cardiovascular health as well as in support of the immune system. An imbalance in these essential fatty acids can lead to poor cholesterol metabolism.

The minerals zinc and copper are both involved in cardiovascular health, and should be provided in a ratio of 5:1 zinc:copper. An imbalance between these two minerals can cause an antagonistic effect of zinc on copper. This effect can interfere with the body's ability to use copper for supporting cardiovascular health. Too much zinc relative to copper can also interfere with the body's ability to manufacture SOD (superoxide dismutase), an important heart-protective enzyme. Also, a proper zinc:copper ratio is required to achieve a proper balance of HDL to LDL. Zinc intake in the typical American man's diet is only 33 to 75 percent of RDA as such dietary supplements that include zinc are contemplated.

Selenium and iodide also have a ratio at which they function most effectively, which is the ratio of selenium to iodide of about 2:1. These minerals affect thyroid function, and therefore also have the resulting effects on metabolism caused by changes in thyroid function. Imbalanced thyroid function can put undue stress on the body that will result in malabsorption of nutrients from food. This, in turn, can retard growth and development.

Pyridoxine, folate and cobalamin also have a ratio at which they function most effectively in the prevention of vascular disorders. The optimal ratio of pyridoxine (vitamin $B_6$) to folate to cobalamin (vitamin $B_{12}$) is about 100:4:1, respectively. These vitamins affect cardiovascular function through their abilities to reduce the levels of the potentially toxic amino acid homocysteine. This ratio recognizes the imbalanced and inadequate levels of these vitamins consumed by individuals at risk of heart disease from their diet.

In addition, vitamin C, vitamin $B_1$ (thiamin), and vitamin E also can be provided. Vitamin C requirements are increased in smokers and cigarette smoking is a major contributor to lung cancer. Vitamin $B_1$ plays an essential role in energy transformation. Thiamin diphosphate (TDP) is a coenzyme necessary for the conversion of carbohydrates to energy. Since U.S. men currently consume about 45% of their total calories from carbohydrates, vitamin $B_1$ optimization in the diet is desirable.

Along with vitamin $B_6$, and vitamin $B_{12}$, folic acid supplementation help modulate blood levels of homocysteine and as such will be useful components in the dietary supplement formulations of the present invention. Vitamin D (calciferol) is essential for formation of the skeleton and for mineral homeostasis. Without vitamin D, the small intestine cannot absorb adequate calcium regardless of how much calcium is available for absorption. Thus, vitamin D is indicated as a component of a nutritional supplement to help build strong bones.

The role of manganese in driving metalloenzyme manganese-superoxide dismutase (Mn-SOD) has been clearly identified, along with a similar role in other metalloenzyme systems (glutamine synthetase, arginase, and pyruvate carboxylase). Numerous enzyme systems have also been shown to undergo manganese activation, even though they are not manganese metalloenzymes. The manganese-SOD connection may be of special clinical importance, since this form of the metalloenzyme appears to be the sole operative form within the cell's mitochondrial membranes, and thus may play a unique role in protection of the mitochondria and assurance of the body's oxidative energy production system. The inclusion of manganese in a dietary supplement would be desirable.

Additional micronutrients that may be included in the supplements include but are not limited to the vitamins such as vitamin A, vitamin C, vitamin E, riboflavin, niacin, niacinamide, pantothenic acid, pyridoxine, cobalamin, biotin, inositol, choline bitartrate, betaine, and vitamin K and minerals such as molybdenum, chromium and potassium.

Stress, exercise, and other conditions create free radicals in the body, which can cause damage to the body's components. To counter the free radicals, the present invention may include the following antioxidants in addition to vitamins C and E discussed above: citrus bioflavonoids, mixed carotenoids, green tea extract, and N-acetylcysteine.

In addition other flavorings and additives well known to those of skill in the art also may be added to the formulations to make them more palatable. For example, formulations may contain ginger, boswellia, fruit flavoring, coloring, preservatives and the like.

When ingested in a solid form, the nutraceutical composition of the invention may additionally contain a solid carrier such as a gelatin or an adjuvant. When administered in liquid form, a liquid carrier such as water, petroleum, oils of animal or plant origin such as peanut oil, mineral oil, soybean oil, or sesame oil, or synthetic oils may be added. The nutraceutical composition of the present invention may also contain stabilizers, preservatives, buffers, antioxidants, or other additives known to those of skill in the art.

EXEMPLIFICATIONS

The invention now being generally described, it will be more readily understood by reference to the following examples, which are included merely for purposes of illustration of certain aspects and embodiments of the present invention, and are not intended to limit the invention. See also FIGS. 24-28 that accompany the examples described below.

Example 1

The Nile rat was used to determine the effect of palm fruit juice (PFJ) on the progression of diabetes. In one study, 8 male diabetic rats and 4 male non-diabetic rats were studied for a 12 week period. The rats were approximately 20 weeks old at the beginning of the experiment, and terminated at approximately 32 weeks of age. Four diabetic rats and 2 non-diabetic rats were given water throughout the experiment, the remaining rats (4 diabetic, 2 non-diabetic) were given PFJ at 1500 ppm gallic acid equivalents (GAE).

Body weight gain and food intake were normal and comparable, although those receiving PFJ ate slightly less while growing slightly better than diabetics not receiving PFJ (Table 1). A plasma lipid profile was established for each Nile rat at 8 months of age (after 12 weeks of the experiment). Blood samples (50 µl) were collected from tail bleeds following light anesthesia ($CO_2+O_2$, 1:1 mixture) and placed into tubes containing EDTA. After separation of plasma, TG and TC were determined spectrophotometrically using Infinity TM kits. In addition, plasma lipoproteins were isolated from larger terminal blood samples using combined Nile rat plasma, 2-3 samples pooled from overnight-fasted rats. Density gradients were prepared in Beckman Ultra-Clear tubes (Beckman Instruments, Palo Alto, Calif.) by successively layering 2 mL of d=1.24 g/mL solution, 3 mL plasma of d=1.21 g/mL solution, 2 mL of d=1.063 g/mL solution, 2.5 mL of d=1.019 g/mL, and 2.5 mL of d=1.006 g/mL solution. Tubes were spun at 37,000 rpm for 48 h at 15° C. in a Beckman SW 41 rotor using a Beckman L-60 optima ultracentrifuge. Following the spin, lipoprotein fractions were collected at preestablished densities: VLDL d<1.006 g/mL, LDL 1.006<d<1.063 g/mL and HDL 1.063<d<1.21 g/mL. Cholesterol for each fraction was determined using an Infinity TM kit.

Non-fasting blood glucose was measured at 0 and 11 weeks, while a fasting value was obtained at week 12 when the rats were sacrificed. Other blood chemistries and organ weights were performed at week 12 as well, as shown in Table 1.

TABLE 1

Diabetic Profile after 12 weeks of palm fruit juice (PFJ) in diabetic and non-diabetic male Nile Rats.

| | Diabetic rats | | Non-diabetic rats | |
| --- | --- | --- | --- | --- |
| | Chow (5020) drink: water n = 4 | Chow (5020) drink: PFJ† n = 4 | Chow (5020) drink: water n = 2 | Chow (5020) drink: PFJ† n = 2 |
| CHO:FAT:Prot % en | 57:21:22 | 57:21:22 | 57:21:22 | 57:21:22 |
| Diet: kcal/g | 3.75 | 3.75 | 3.75 | 3.75 |
| Body weight (g) | | | | |
| Initial (age: ca. 20 wks) | 90 ± 24 | 92 ± 12 | 76 ± 1 | 77 ± 1 |
| Final (12 wk) | 92 ± 14 | 110 ± 14 | 128 ± 9 | 109 ± 4 |
| Body wt gain (g/day) | 0.013 ± 0.168 | 0.133 ± 0.043 | 0.415 ± 0.064 | 0.255 ± 0.049 |
| Food intake - final 4 wks (g/d) | 15.2 ± 5.3 | 12.4 ± 1.0 | 13.1 ± 1.7 | 14.9 ± 2.6 |
| (kcal/d) | 57 ± 20 | 46 ± 4 | 49 ± 6 | 56 ± 10 |
| (kcal/d/kg BW) | 620 | 418 | 323 | 514 |
| Drink intake - final 4 wks (ml/d) | | | | |
| Water | 116 ± 17 | 0 | 20 ± 5 | 0 |
| Juice | 0 | 95 ± 18 | 0 | 64 ± 14 |
| GAE intake (mg/kg BW/d) | 0 | 1408 ± 272 | 0 | 1039 ± 231 |
| Organ weight (% BW) | | | | |
| Liver | 6.84 ± 1.20 | 2.05 ± 0.35* | 3.12 ± 0.08 | 3.21 ± 0.15 |
| Kidney | 2.05 ± 0.35 | 1.12 ± 0.11* | 0.79 ± 0.01 | 0.79 ± 0.06 |
| Cecum | 5.00 ± 1.86 | 3.56 ± 0.66 | 1.21 ± 0.10 | 1.55 ± 0.09 |
| Adipose | | | | |
| Perirenal | 0.18 ± 0.21 | 0.55 ± 0.31 | 1.38 ± 0.23 | 1.16 ± 1.00 |
| Epididymal | 0.76 ± 0.98 | 2.02 ± 0.52 | 3.00 ± 0.41 | 2.25 ± 0.39 |
| Inguinal | 0.14 ± 0.28 | 0.65 ± 0.12* | 0.88 ± 0.04 | 0.95 ± 0.37 |
| Length (cm) | 13.5 ± 0.7 | 14.8 ± 0.4* | 14.3 ± 0.4 | 14.8 ± 0.4 |
| BMI (kg/m$^2$) | 5.01 ± 0.55 | 4.98 ± 0.39 | 6.27 ± 0.14 | 5.01 ± 0.05 |
| LMI (kg/m$^2$) | N/A | N/A | N/A | N/A |

TABLE 1-continued

Diabetic Profile after 12 weeks of palm fruit juice (PFJ) in diabetic and non-diabetic male Nile Rats.

| | Diabetic rats | | Non-diabetic rats | |
|---|---|---|---|---|
| | Chow (5020) drink: water n = 4 | Chow (5020) drink: PFJ† n = 4 | Chow (5020) drink: water n = 2 | Chow (5020) drink: PFJ† n = 2 |
| Glucose (mg/dL) | | | | |
| Non-fasting B Glucose at 0 wk | 314 ± 161 | 313 ± 202 | 109 ± 15 | 125 ± 3 |
| Non-fasting B Glucose at 11 wks | 388 ± 86 | 306 ± 84 | 65 ± 23 | 44 ± 3 |
| Fasting Plasma Glucose at 12 wks | 659 ± 299 | 121 ± 37* | 87 ± 11 | 86 ± 4 |
| Plasma (fasting, terminal) | | | | |
| TG (mg/dL) | 2369 ± 1724 | 117 ± 42* | 52 ± 1 | 78 ± 10 |
| TC (mg/dL) | 763 ± 377 | 144 ± 39* | 109 ± 46 | 104 ± 15 |
| VLDL-C (mg/dl)¶ | 571 ± 473 | 21 ± 6 | 34 | 31 |
| LDL-C (mg/dl)¶ | 216 ± 31 | 39 ± 25* | 34 | 33 |
| HDL-C (mg/dl)¶ | 23 ± 18 | 83 ± 29 | 47 | 39 |
| LDL-C/HDL-C ratio | 13.0 ± 8.8 | 0.44 ± 0.20* | 0.72 | 0.83 |
| TC/HDL-C ratio | 39.0 ± 7.0 | 1.7 ± 0.1* | 2.43 | 2.63 |

Values are mean ± SD (n = 2-4)
*Significantly different (p < 0.05). Diabetic rat groups compared to nondiabetic.
†Palm fruit juice diluted 1:1 with water (GAE = 1500 ppm)
¶Lipoproteins from pooled plasma (diabetic rats n = 2, non-diabetics n = 1 for each category)

Non-fasting blood glucose levels at the start of the experiment were about 3 times greater in the diabetic rats than the non-diabetic controls (300+ vs. 100+mg/dL). After 12 weeks, the fasting plasma glucose was 650 mg/dL in the diabetic rats fed with water (diabetic controls), but only 120 mg/dL in the diabetic rats given PFJ. In the non-diabetic rats, both the water and PFJ groups had fasting blood glucose<100 mg/dL that did not significantly differ from each other.

Plasma lipids and lipoproteins at the end of the 12 week study differed between the diabetic rats given water or PFJ. The diabetic rats on water had severely elevated triglycerides and VLDL-C, and depressed HDL-C. The diabetic rats given PFJ had plasma lipid values that were essentially normal and nearly identical to the non-diabetic controls.

At necropsy, the wasting of fat depots associated with advanced diabetes in rats given water was not observed in the palm fruit juice group, which were similar to the nondiabetic rats. Further, the increase in liver and kidney size of diabetics on water was normalized by the supplement of PFJ in diabetics (Table 1).

Thus, providing palm fruit juice at 1500 ppm GAE as the sole water source was able to deter diabetes progression in older (20 weeks of age), moderately diabetic male Nile rats as evidenced by improved blood glucose and lipid profiles (especially VLDL and HDL). Unsupplemented diabetic rats progressed to severe polyuria/polydipsia (6-fold increase in water intake) with enlarged kidneys and liver and marked elevation in terminal glucose, TG, and TC with depressed HDL.

Example 2

A study was conducted using 16 young (12 week old), healthy male Nile rats with normal blood glucose (50-55 mg/dL) to determine whether long term PFJ intake would deter onset or even prevent diabetes. Animals were fed standard rat chow #5020 for 9 months along with either water or palm fruit juice (1500 ppm GAE). At the end of the 9 mo period, the fasting blood glucose was elevated 2.5× in rats given water compared to the rats given PFJ, which had a normal mean value<80 mg/dL (Table 2).

TABLE 2

Diabetic profile after 9 months ± PFJ in male Nile rats.

| | Group 1 (control, n = 8) | Group 2 (experimental, n = 8) |
|---|---|---|
| Diet | | |
| Food | Chow (5020) | Chow (5020) |
| Drink | water | PFJ† |
| Body Weight (g) | | |
| Initial (age: 12 wk) | 94 ± 14 | 95 ± 15 |
| After 3 mo | 119 ± 15 | 128 ± 19 |
| After 7 mo. | 124 ± 13 | 130 ± 19 |
| Terminal (9 mo.) | 124 ± 12 | 131 ± 17 |
| Body weight gain (g/d) | 0.11 ± 0.06 | 0.14 ± 0.05 |
| Food Intake | | |
| (g/d) 1st mo. | 16 ± 5 | 10 ± 2* |
| (g/d) at 7th mo. | 23 ± 8 | 12 ± 1* |
| (g/d) at 9th mo. | 20 ± 5 | 11 ± 1* |
| (kcal/d) at 1st mo. | 60 ± 19 | 38 ± 8 |
| (kcal/d) at 7th mo. | 86 ± 30 | 45 ± 4 |
| (kcal/d) at 9th mo. | 75 ± 19 | 41 ± 4 |
| Water or PFJ intake | | |
| (ml/d) 1st mo. | 32 ± 19 | 53 ± 4* |
| (ml/d) 7th mo. | 50 ± 20 | 55 ± 11 |
| (ml/d) 9 mo. | 68 ± 25 | 68 ± 11 |
| (kcal/d) at 1st mo. | 0 | 15 ± 1 |
| (kcal/d) at 7th mo. | 0 | 16 ± 2 |
| (kcal/d) at 9th mo. | 0 | 19 ± 3 |
| Total energy intake (food + drink, 9th mo) | | |
| (kcal/d) | 75 | 60 |
| GAE intake, in 9th mo. (mg/kg BW/d) | 0 | 779 |
| Nonfasting Blood glucose (mg/dL) | | |
| At 9 mo. | 401 ± 139 | 199 ± 100* |
| Fasting Blood Glucose (mg/dL) | | |
| Initial | 54 ± 14 | 53 ± 25 |
| After 3 mo | 136 ± 112 | 39 ± 9* |

TABLE 2-continued

Diabetic profile after 9 months ± PFJ in male Nile rats.

|  | Group 1 (control, n = 8) | Group 2 (experimental, n = 8) |
|---|---|---|
| After 7 mo | 144 ± 102 | 72 ± 26 |
| Terminal (after 9 mo.) | 190 ± 108 | 78 ± 57* |
| Organ weight (% BW) | | |
| Liver** | 6.30 ± 1.25 | 4.64 ± 0.89* |
| Spleen | 0.15 ± 0.05 | 0.18 ± 0.05 |
| Cecum | 2.67 ± 1.11 | 1.73 ± 0.51* |
| Kidney | 1.30 ± 0.32 | 0.99 ± 0.10* |
| Adipose | | |
| Epididymal | 2.58 ± 0.95 | 2.84 ± 0.51 |
| Perirenal | 0.82 ± 0.44 | 1.27 ± 0.45 |
| Inguinal | 0.84 ± 0.11 | 1.03 ± 0.19* |
| Omental | 0.89 ± 0.21 | 0.90 ± 0.24 |
| Scapula Brown Fat | 1.53 ± 0.73 | 1.78 ± 0.49 |
| Total (all above) | 6.66 ± 1.67 | 7.82 ± 1.47 |
| Adrenals | 0.047 ± 0.019 | 0.050 ± 0.021 |
| Pancreas | 0.42 ± 0.05 | 0.40 ± 0.13 |
| Heart | 0.32 ± 0.04 | 0.30 ± 0.04 |
| Thymus | 0.11 ± 0.01 | 0.14 ± 0.04 |
| Testicles | 1.53 ± 0.15 | 1.46 ± 0.24 |
| Brain | 0.71 ± 0.06 | 0.68 ± 0.07 |
| Carcass | 67 ± 3 | 70 ± 2 |
| Body length (cm) | 14.1 ± 0.2 | 14.2 ± 0.6 |
| BMI (Kg/m$^2$) | 6.2 ± 0.5 | 6.4 ± 0.4 |
| LMI (Kg/m$^2$) | 4.2 ± 0.4 | 4.5 ± 0.3 |
| Plasma TC (mg/dL) | | |
| Terminal (9 mo.) | 361 ± 155 | 221 ± 98* |
| Plasma TG (mg/dL) | | |
| Initial | 75 ± 20 | 75 ± 24 |
| After 3 mo. | 53 ± 23 | 57 ± 25 |
| After 7 mo. | 196 ± 104 | 107 ± 54* |
| Terminal (9 mo.) | 585 ± 616 | 111 ± 67* |

Values are represented as mean ± SD
†Palm fruit juice diluted with water to GAE = 1500 ppm.
*Significantly (P < 0.05) different
**In PFJ group, 4/8 livers had pale nodules.

At the end of the study, rats fed with water only had elevated triglycerides and total cholesterol levels in addition to the increased blood glucose compared to the rats fed PFJ.

The water-fed rats also exhibited hepatomegaly and nephromegaly. The water-fed group exhibited other diabetic symptoms including polydipsia and polyphagia.

Total caloric intake during the 9$^{th}$ month was 20% greater in diabetics and their water intake doubled over the 9 month period. Nonetheless, those given PFJ and consuming fewer calories grew the same as the diabetics (body weight, length, BMI, LMI), revealing the caloric over consumption (wastage) often associated with the diabetes in these rats. Palm fruit juice-supplemented Nile rats drank more from the beginning, presumably due to the sugar content of PFJ (a subsequent study shows that they favor sugared drinks). However, this group showed minimal increase in drinking over time, unlike the diabetic polydipsia that developed in the control (diabetic) group. Rats given PFJ had smaller kidneys and livers than rats without PFJ, which developed diabetes.

Chronic PFJ at 1500 ppm GAE showed no detrimental effects on growth or organ weight. Total body fat was not affected in either group, and total fat reserves were not depleted by diabetes, as the disease was not as severe in these 8 rats given water compared to Example 1 rats.

The plasma triglycerides were elevated by 7 months and rose dramatically between 7-9 months as diabetes developed in rats given water, indicating that several rats in this group were beginning to reach advanced disease. Thus, long-term intake of PFJ at 1500 ppm in healthy, young Nile rats protected them against diabetes onset, as measured by glucose, blood lipids, and weight of livers and kidneys.

Example 3

A study was conducted to determine the effect of graded concentrations of PFJ intake on diabetes progression in Nile rats. Twenty-eight young (12 weeks old), healthy male Nile rats were separated into four groups. The first group (control) was only given water during the 17 week study period. The second, third, and fourth groups were given palm fruit juice at 450 ppm, 900 ppm, and 1800 ppm GAE, respectively, throughout the study. All groups were fed standard rat chow #5020. After 17 weeks, the rats were sacrificed and measurements were added to those of body weight and food intake, taken throughout the study. Results are shown in Table 3

TABLE 3

Body weight, blood glucose and plasma lipids of 12 wk old male Nile rats fed chow and drinking water or graded doses of palm fruit juice for 17 weeks.

|  | Chow 5020 | | | |
|---|---|---|---|---|
|  | Water | PFJ 450 GAE | PFJ 900 GAE | PFJ 1800 GAE |
| CHO:FAT:Prot % en | 57:21:22 | 57:21:22 | 57:21:22 | 57:21:22 |
| Diet: Kcal/g | 3.75 | 3.75 | 3.75 | 3.75 |
| Body weight (g) | | | | |
| Initial (11-13 wks old) | 95 ± 20 | 98 ± 24 | 95 ± 14 | 98 ± 12 |
| After 9 wk | 108 ± 18 | 116 ± 22 | 111 ± 19 | 110 ± 15 |
| After 16 wk | 107 ± 19 | 116 ± 26 | 117 ± 19 | 120 ± 21 |
| Final 17 wk | 111 ± 18 | 122 ± 22 | 117 ± 18 | 118 ± 20 |
| Body wt. Gain (g/d) | 0.16 ± 0.21 | 0.32 ± 0.17 | 0.32 ± 0.17 | 0.29 ± 0.24 |
| Food Intake | | | | |
| during wk 3-4 (g/d) | 14.3 ± 3.4 | 15.0 ± 6.8 | 12.0 ± 2.7 | 12.8 ± 3.6 |
| during wk 10-11 (g/d) | 21.6 ± 9.3$^{a,b,c}$ | 14.2 ± 2.1$^a$ | 13.3 ± 2.5$^b$ | 12.5 ± 2.7$^c$ |
| during wk 14-15 (g/d) | 19.8 ± 7.9$^{a,b,c}$ | 14.5 ± 4.0$^a$ | 11.7 ± 2.6$^b$ | 10.4 ± 2.4$^c$ |
| over all (g/d) | 17.7 ± 4.7$^{a,b}$ | 14.4 ± 4.3 | 12.2 ± 1.9$^a$ | 11.8 ± 2.6$^b$ |
| (kcal/d) | 66 ± 18$^{a,b}$ | 54 ± 16 | 46 ± 7$^a$ | 44 ± 10$^b$ |
| (kcal/d/kg BW) | 609 ± 194$^{a,b,c}$ | 410 ± 73$^a$ | 407 ± 116$^b$ | 381 ± 101$^c$ |
| Water or juice intake | | | | |
| (mL/d) 1st mo | 26 ± 8$^{a,b,c}$ | 42 ± 15$^{a,c}$ | 50 ± 16$^b$ | 54 ± 8$^c$ |
| (mL/d) 2nd mo | 42 ± 25 | 45 ± 17 | 42 ± 11 | 37 ± 10 |

TABLE 3-continued

Body weight, blood glucose and plasma lipids of 12 wk old male Nile rats fed chow and drinking water or graded doses of palm fruit juice for 17 weeks.

| | Chow 5020 | | | |
|---|---|---|---|---|
| | Water | PFJ 450 GAE | PFJ 900 GAE | PFJ 1800 GAE |
| (mL/d) 3rd mo | 66 ± 34 | 62 ± 26 | 55 ± 20 | 40 ± 21 |
| (kcal/d) 3rd mo | 0 | 4 ± 1 | 8 ± 3 | 11 ± 6 |
| Total energy intake | | | | |
| food + juice (Kcal/d) | 66 ± 18 | 58 ± 16 | 53 ± 7 | 55 ± 10 |
| GAE intake, 3rd mo. (mg/kg BW/d) | 0 | 229 | 423 | 508 |
| Organ weight (% BW) | | | | |
| Liver | $5.40 ± 1.37^{a,b}$ | 4.51 ± 0.90 | $4.29 ± 1.04^a$ | $3.84 ± 0.63^b$ |
| Spleen | 0.24 ± 0.25 | 0.15 ± 0.04 | 0.12 ± 0.02 | 0.14 ± 0.02 |
| Cecum | 1.99 ± 1.37 | 1.98 ± 0.46 | 1.51 ± 0.38 | 1.73 ± 1.13 |
| Kidney | $1.43 ± 0.69^{a,b,c}$ | $1.01 ± 0.21^a$ | $0.94 ± 0.21^b$ | $0.91 ± 0.22^c$ |
| Adipose | | | | |
| Epididymal | 2.51 ± 0.74 | 2.37 ± 1.12 | 2.99 ± 0.85 | 2.93 ± 1.30 |
| Perirenal | 0.81 ± 0.37 | 0.84 ± 0.61 | 1.26 ± 0.52 | 1.29 ± 0.55 |
| Inguinal | 0.76 ± 0.24 | 0.74 ± 0.25 | 0.91 ± 0.14 | 0.93 ± 0.26 |
| Omental | 0.89 ± 0.25 | 1.07 ± 0.43 | 0.95 ± 0.32 | 1.12 ± 0.34 |
| Scapula Brown Fat | 1.30 ± 0.88 | 1.60 ± 1.36 | 1.68 ± 0.62 | 2.02 ± 0.84 |
| Total (all above) | 6.26 ± 1.03 | 6.63 ± 3.30 | 7.79 ± 1.98 | 8.29 ± 3.03 |
| Adrenals | 0.048 ± 0.021 | 0.041 ± 0.007 | 0.035 ± 0.008 | 0.049 ± 0.010 |
| Pancreas | 0.49 ± 0.06 | $0.47 ± 0.03^{a,b}$ | $0.61 ± 0.17^a$ | $0.62 ± 0.14^b$ |
| Heart | 0.34 ± 0.04 | 0.32 ± 0.05 | 0.32 ± 0.06 | 0.30 ± 0.04 |
| Thymus | 0.10 ± 0.05 | 0.09 ± 0.03 | 0.13 ± 0.04 | 0.12 ± 0.04 |
| Testicles | 1.34 ± 0.22 | 1.36 ± 0.32 | 1.49 ± 0.30 | 1.30 ± 0.36 |
| Carcass | 68 ± 2 | 66 ± 8 | 70 ± 3 | 70 ± 1 |
| Body length (cm) | 13.9 ± 0.6 | 14.1 ± 0.6 | 14.1 ± 0.6 | 13.9 ± 0.6 |
| BMI (Kg/m2) | 5.71 ± 0.56 | 6.16 ± 0.77 | 5.87 ± 0.51 | 6.08 ± 0.91 |
| LMI (Kg/m2) | 3.90 ± 0.26 | 4.04 ± 0.55 | 4.09 ± 0.28 | 4.26 ± 0.64 |
| Blood glucose (fasting)(mg/dL) | | | | |
| Initial (0 time, GTT) | 87 ± 96 | 69 ± 40 | 68 ± 44 | 125 ± 150 |
| 1 hr (GTT) | 285 ± 153 | 272 ± 176 | 263 ± 198 | 268 ± 187 |
| After 9 wk | $175 ± 145^{a,b,c}$ | $79 ± 40^a$ | $78 ± 62^b$ | $34 ± 6^c$ |
| After 16 wk | $180 ± 130^{a,b}$ | $147 ± 117^c$ | $82 ± 58^a$ | $45 ± 17^{b,c}$ |
| Final 17 wk (0 time, GTT) | $126 ± 120^a$ | 82 ± 51 | 67 ± 34 | $52 ± 21^a$ |
| 1 hr (GTT) | 350 ± 191 | 481 ± 182 | 354 ± 139 | 342 ± 133 |
| Final Av of 16 + 17 wk | $139 ± 109^{a,b}$ | 95 ± 50 | $74 ± 46^a$ | $48 ± 16^b$ |
| Final plasma insulin (ng/mL) | $3.38 ± 1.57^a$ | $1.63 ± 1.29^{b,c}$ | $5.71 ± 1.56^b$ | $6.20 ± 2.43^{a,c}$ |
| Liver lipids | | | | |
| TC (mg/g) | 21.1 ± 8.6 | 18.4 ± 9.2 | 21.7 ± 8.6 | 24.3 ± 10.7 |
| TG (mg/g) | $51.4 ± 33.3^{a,b}$ | $52.7 ± 16.9^c$ | $84.4 ± 23.7^{a,c}$ | $81.8 ± 32.7^b$ |
| Plasma | | | | |
| TC (mg/dL) | | | | |
| Final 17 wk | $401 ± 238^{a,b,c}$ | $193 ± 35^a$ | $154 ± 39^b$ | $172 ± 78^c$ |
| TG (mg/dL) | | | | |
| Initial | 85 ± 35 | 82 ± 46 | 85 ± 18 | 99 ± 102 |
| Final 17 wk | $224 ± 189^{a,b,c}$ | $116 ± 70^a$ | $86 ± 47^b$ | $65 ± 30^c$ |
| Urine | | | | |
| PH, final 17 wk | 6.2 ± 0.4 | $6.1 ± 0.2^a$ | 6.6 ± 0.3 | $6.7 ± 0.8^a$ |
| Protein, final 17 wk (mg/dL) | 118 ± 106 | 58 ± 46 | 98 ± 136 | 130 ± 97 |

Values are mean ± SD (n = 6-7)
GTT = Glucose Tolerance Test
PFJ = Palm Fruit Juice
GAE = Gallic Acid Equivalent
[a,b,c]Means in a row sharing a common superscript are significantly different (p < 0.05) using one-way ANOVA and Fisher's PLSD test.

Rats in all groups grew to approximately the same length and weight (calculated as BMI and LMI), although the control (water) group weighed slightly less at the end and this group had nephromegaly, associated with increased water intake that was obvious by week 12. Control rats also ate more, presumably to compensate for loss of glucose in the urine or for failed glucose utilization by tissues. Kidney weight had an inverse relationship to PFJ intake, but seemed to plateau at 900 GAE. No difference was found for adipose weight between groups. Elevated blood glucose observed in the control rats indicated that the onset of diabetes was prior to week 9. As in previous studies, hepatomegaly was observed terminally in the water group, and liver weight and blood glucose decreased as the concentration of PFJ increased, with normal values found at 900 GAE and above. Even 450 GAE had a significant lowering effect on plasma total cholesterol and triglycerides, which was only slightly improved at 900 GAE and 1800 GAE.

The data demonstrates that PFJ helps to protect against the development and progression of Type 2 diabetes, with the protective effect essentially complete at 900 GAE. A dose-dependent effect on some blood chemistries did occur, but not for all measurements.

Example 4

A fourth study was conducted to determine the effect of PFJ on 11 older (28 week old) male Nile rats with early diabetes (mean glucose>110 mg/dL). One group of rats was given a water-only diet, and the other group received PFJ at 1500 ppm GAE for 20 weeks (5 months). Both groups were fed standard rat chow #5020 (Table 4).

TABLE 4

Diabetic profile after 20 weeks on PFJ in male Nile rats.

| | Diet | |
|---|---|---|
| | Chow (5020) drink: water | Chow (5020) drink: PFJ† |
| CHO:FAT:Prot % en | 57:21:22 | 57:21:22 |
| Diet: Kcal/g | 3.75 | 3.75 |
| Body weight (g) | | |
| Initial (age: 28 wk) | 135 ± 38 | 125 ± 19 |
| After 12 wk | 149 ± 24 | 120 ± 11 |
| Final, 20 wk | 140 ± 24 | 116 ± 13 |
| Carcas weight (g) | 90 ± 16 | 78 ± 7 |
| Body length (cm) | 14.8 ± 0.4 | 14.2 ± 0.2* |
| BMI (Kg/m2) | 6.4 ± 0.6 | 5.8 ± 0.5 |
| LMI (Kg/m2) | 4.1 ± 0.6 | 3.9 ± 0.3 |
| Food intake | | |
| (g/d) | 21 ± 4 | 13 ± 1 |
| (kcal/d) | 79 ± 14 | 47 ± 5 |
| Drink intake (ml/d) | | |
| Water | 85 ± 21 | |
| Juice | | 68 ± 11* |
| Kcal with juice per day | 0 | 19 ± 3 |
| Total energy intak (food + drink) | | |
| kcal/d | 79 ± 14 | 66 ± 8 |
| GAE intake (mg/kg BW/d) | 0 | 879 ± 142 |
| Organ weight (% BW) | | |
| Liver | 7.75 ± 1.78 | 5.80 ± 1.00* |
| Spleen | 0.153 ± 0.037 | 0.154 ± 0.032 |
| Cecum | 2.28 ± 0.55 | 2.43 ± 0.73 |
| Kidney | 1.42 ± 0.41 | 1.13 ± 0.20 |
| Adipose | | |
| Epididymal | 2.98 ± 0.92 | 2.18 ± 0.98 |
| Perirenal | 0.93 ± 0.42 | 0.76 ± 0.57 |
| Inguinal | 0.83 ± 0.29 | 0.71 ± 0.19 |
| Omental | 1.14 ± 0.41 | 0.74 ± 0.25 |
| Scapula Brown Fat | 1.41 ± 0.40 | 1.30 ± 0.44 |
| Total (all above) | 7.30 ± 2.14 | 5.69 ± 2.01 |
| Adrenals | 0.042 ± 0.002 | 0.044 ± 0.009 |
| Pancreas | 0.208 ± 0.069 | 0.264 ± 0.073 |
| Pancreas fat | 0.446 ± 0.129 | 0.223 ± 0.132* |
| Heart | 0.319 ± 0.035 | 0.319 ± 0.042 |
| Thymus | 0.114 ± 0.015 | 0.085 ± 0.016* |
| Testicles | 1.30 ± 0.48 | 1.37 ± 0.20 |
| Brain | 0.63 ± 0.06 | 0.71 ± 0.05* |
| Fast B. Glucose at 0 wk (mg/dL) | 97 ± 24 | 124 ± 83 |
| Nonfast B. Glucose at 0 wk (mg/dL) | 396 ± 137 | 406 ± 124 |
| Nonfast B. Glucose at 12 wk (mg/dL) | 423 ± 88 | 294 ± 134 |
| Fast B. Glucose at 20 wk (mg/dL) | 270 ± 188 | 125 ± 75 |
| delta Fast B. Glucose 0-20 wk (mg/dL) | 173 ± 168 | 1 ± 59* |
| GTT after 20 wk (mg/dL) | | |
| 0 time | 270 ± 188 | 125 ± 75 |
| After 1 h | 587 ± 98 | 381 ± 178* |
| After 3 h | 344 ± 259 | 194 ± 185 |
| Plasma TC (mg/dL) | | |
| Initial | 719 ± 999 | 723 ± 512 |
| Final, 20 wk | 558 ± 408 | 390 ± 110 |
| Plasma TG (mg/dL) | | |
| Initial | 200 ± 96 | 336 ± 172 |
| Final, 20 wk | 652 ± 488 | 108 ± 60* |
| Liver lipids | | |
| TC (mg/g) | 9.5 ± 5.1 | 15.0 ± 0.4* |
| TG (mg/g) | 7.7 ± 3.6 | 12.4 ± 3.7 |

Values are mean ± SD (n = 5-6)
†Palm fruit juice diluted with water (GAE = 1500 ppm)
*Significantly different (p < 0.05)

As in earlier studies, food intake was lower in the PFJ rats, which were slightly smaller and lost weight during the study while the diabetics gained weight. However, caloric reduction was compensated somewhat by the natural sugar in the juice so that energy intake reduction (15%) was not significant. In the final analysis, the PFJ-fed rats were shorter with a tendency for lower BMI and LMI. Following the 20 week period, the rats given PFJ had less polydipsia and polyphagia, suggesting an improvement in diabetes symptoms. Livers were significantly smaller in PFJ-supplemented rats, but a tendency for smaller kidneys was not statistically significant compared to rats given water only. In addition, the water group showed a blood glucose increase of nearly 200 mg/dL over the 20 week period, whereas blood glucose was unchanged in the PFJ group. More striking results were seen in the fasting plasma total cholesterol (TC), which decreased 22% and 46% in the water and PFJ groups, respectively, over the 20 week period. More striking was the 3-fold increase in plasma triglycerides in the water group, in contrast to the nearly 70% decrease to normal values in the PFJ group.

Thus, even in older male Nile rats showing diabetes onset, supplementation with PFJ at 1500 ppm GAE was capable of deterring further diabetes advancement or actually improved various diabetic indices, especially blood glucose and plasma triglycerides.

Supplementing PFJ rich in phenolics at 450-1800 ppm GAE, showed a dose-related protective effect against development of type 2 diabetes in the Nile rat model. Specifically, PFJ maintained a lower glucose and prevented the glucose increase in young Nile rats, and triglycerides also were prevented from increasing in naive rats, or even declined in some cases in rats with modest diabetes. PFJ resulted in less food and water intake and protected against kidney enlargement and end-stage nephritis. Without being bound by theory, the hypothesis is that one or more phenolics (or some other unidentified component) in PFJ acted as potent water-soluble antioxidant(s) in pancreatic β-cells to protect mitochondria from reactive oxygen species (ROS) that ultimately destroy β-cells in unsupplemented rats. In essence, the Nile rat is unusually prone to excessive wear and tear on insulin production when faced with the ample energy supply in a commercial or purified diet.

EQUIVALENTS

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

INCORPORATION BY REFERENCE

All of the US Patents and US Patent Application Publications cited herein are hereby incorporated by reference.

What is claimed is:

1. A method of treating a metabolic imbalance in a mammal in need thereof comprising administering to the mammal a therapeutically effective amount of an extract from a fruit of genus *Elaeis*, wherein said extract is a water-soluble extract obtained from the vegetation liquor of a palm oil milling process, and wherein said metabolic imbalance is selected from the group consisting of: diabetes mellitus, gestational diabetes, genetic defects of β-cell function, genetic defects in insulin action, diseases of the pancreas, other genetic syndromes associated with diabetes, a pre-diabetic state and metabolic syndrome.

2. The method of claim 1, wherein said extract is in a nutraceutical or pharmaceutical composition.

3. The method of claim 1, wherein said water-soluble extract contains phenolics.

4. The method of claim 3, wherein said phenolics include cinnamate and benzoate derivatives.

5. The method of claim 1, wherein treating the metabolic imbalance further comprises enhancing an insulin secretion or sensitivity.

6. The method of claim 1, wherein treating the metabolic imbalance further comprises reducing a blood glucose level.

7. The method of claim 1, wherein the metabolic imbalance is diabetes mellitus.

8. The method of claim 7, wherein diabetes mellitus is type I.

9. The method of claim 7, wherein diabetes mellitus is type II.

10. The method of claim 7, wherein diabetes mellitus is Latent Autoimmune Diabetes in adults.

11. The method of claim 1, wherein the metabolic imbalance is metabolic syndrome.

12. The method of claim 11, wherein treating metabolic syndrome comprises treating one or more diagnostic criteria.

13. The method of claim 12, wherein said diagnostic criteria is selected from the group consisting of waist circumference, triglycerides, HDL, blood pressure, and fasting blood glucose level.

14. The method of claim 1, wherein the metabolic imbalance is pre-diabetic state and the mammal has one or more risk factors for diabetes mellitus.

15. The method of claim 14, wherein the pre-diabetic state comprises impaired fasting glucose level or glucose intolerance.

16. The method of claim 14, wherein said one or more risk factors for diabetes mellitus is selected from the group consisting of: age, physical inactivity, abnormal BMI, genetic predisposition, ethnicity, hypertension, polycystic ovary syndrome, cardiovascular disease, previous impaired fasting glucose or glucose tolerance, and other clinical conditions associated with insulin resistance.

* * * * *